(12) United States Patent
Yoshikawa et al.

(10) Patent No.: US 7,897,042 B2
(45) Date of Patent: *Mar. 1, 2011

(54) ENTRAPPING IMMOBILIZATION PELLETS FOR PURIFYING BREEDING WATER, PROCESS AND APPARATUS FOR PURIFYING BREEDING WATER, AND AQUARIUM SET

(75) Inventors: Shinichi Yoshikawa, Tokyo (JP); Naoki Abe, Tokyo (JP); Kazuichi Isaka, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/382,740

(22) Filed: Mar. 23, 2009

(65) Prior Publication Data

US 2009/0188858 A1 Jul. 30, 2009

Related U.S. Application Data

(62) Division of application No. 11/812,756, filed on Jun. 21, 2007, now Pat. No. 7,794,590.

(30) Foreign Application Priority Data

Jun. 28, 2006 (JP) .............................. 2006-178512

(51) Int. Cl.
- A01K 63/04 (2006.01)
- C02F 3/08 (2006.01)
- C12N 11/04 (2006.01)
- C12N 11/08 (2006.01)

(52) U.S. Cl. ............... 210/151; 210/167.22; 210/416.2; 210/615; 119/260; 435/180; 435/182

(58) Field of Classification Search .................. 210/150, 210/151, 167.21, 167.22, 416.2, 615–617; 119/260, 261; 435/180, 182
See application file for complete search history.

(56) References Cited

U.S. PATENT DOCUMENTS

| | | | |
|---|---|---|---|
| 4,138,292 A | * | 2/1979 | Chibata et al. ............... 435/178 |
| 6,080,304 A | | 6/2000 | Gomi |
| 6,158,386 A | | 12/2000 | Limcaco |
| 6,297,033 B1 | | 10/2001 | Van Rijn et al. |
| 6,403,028 B1 | * | 6/2002 | Colby et al. ................... 422/15 |
| 2003/0178363 A1 | * | 9/2003 | Sato et al. ..................... 210/618 |
| 2004/0101944 A1 | | 5/2004 | Willuweit et al. |

FOREIGN PATENT DOCUMENTS

| | | |
|---|---|---|
| JP | A-8-57494 | 3/1996 |
| JP | A-2003-094082 | 4/2003 |
| JP | A-2005-117925 | 5/2005 |
| WO | WO-2004/071969 A1 | 8/2004 |

OTHER PUBLICATIONS

Extended European Search Report of EP 07012507 issued on Oct. 14, 2009.
Feb. 18, 2010 Office Action issued in U.S. Appl. No. 11/812,756.
Nov. 27, 2009 Office Action issued in U.S. Appl. No. 11/812,756.
May 4, 2009 Office Action issued in U.S. Appl. No. 11/812,756.

* cited by examiner

*Primary Examiner*—Fred Prince
(74) *Attorney, Agent, or Firm*—Oliff & Berridge, PLC

(57) ABSTRACT

Entrapping immobilization pellets for purifying breeding water in an aquarium to breed aquatic animals, wherein the entrapping immobilization pellets have a phosphorus content of 0.05 mass % or less.

11 Claims, 19 Drawing Sheets

_US 7,897,042 B2_

ENTRAPPING IMMOBILIZATION PELLETS FOR PURIFYING BREEDING WATER, PROCESS AND APPARATUS FOR PURIFYING BREEDING WATER, AND AQUARIUM SET

BACKGROUND OF THE INVENTION

This is a Divisional of application Ser. No. 11/812,756 filed Jun. 21, 2007, now U.S. Pat. No. 7,794,590, which claims the benefit of Japanese Patent Application No. 2006-178512 filed Jun. 28, 2006. The disclosures of the prior applications are hereby incorporated by reference herein in their entirety.

FIELD OF THE INVENTION

The present invention relates to entrapping immobilization pellets for purifying breeding water, a process and an apparatus for purifying breeding water, and an aquarium set. More particularly, the present invention relates to entrapping immobilization pellets for purifying breeding water which remove ammonium nitrogen contained in breeding water to breed aquatic animals by decomposition of microorganisms and improve the beauty; a process and an apparatus for purifying breeding water; and an aquarium set.

DESCRIPTION OF THE RELATED ART

Conventionally, attachment-type purification materials in which nitrifying bacteria (ammonium oxidizing bacteria or nitrite oxidizing bacteria) are naturally attached to filters, sponges, porous ceramics, or the like have been used as materials for removing ammonium nitrogen or nitrite nitrogen contained in aquaria to breed aquatic animals. Such attachment-type purification materials are formed by placing filters, sponges, porous ceramics, or the like in aquaria or in external apparatuses in which breeding water is circulated and bringing them into contact with breeding water.

An attachment-type purification material generally does not have purification performance to remove ammonium nitrogen, nitrite nitrogen, or the like contained in breeding water until nitrifying bacteria are sufficiently attached onto the material. Therefore, the problem is that the ammonium nitrogen concentration in breeding water is increased until nitrifying bacteria are sufficiently attached onto the material.

Specifically, it usually takes about two to four weeks to make nitrifying bacteria attached to the material so that the material can treat ammonium nitrogen. Even if the material can treat ammonium nitrogen, the material can oxidize ammonium nitrogen only to nitrite at the initial stage, and nitrite nitrogen more toxic than ammonium nitrogen is easily accumulated in breeding water. It takes about further two to four weeks to make nitrite oxidizing bacteria attached to the material and thus oxidize nitrite nitrogen to nitrate nitrogen having relatively small toxicity. That is, water quality is not favorable for aquatic animals for two weeks to two months after placing the material in an aquarium.

For example, Japanese Patent Application Laid-Open No. 2005-117925 proposes, as measures against this problem, a filter for purifying an aquarium for fish and aquatic animals obtained by immersing carbonized cotton in a purification tank where nitrifying bacteria are grown, so that the nitrifying bacteria are naturally attached to and immobilized in the carbonized cotton, and converting the carbonized cotton into a sheet. This patent specification describes that a filter to which nitrifying bacteria are previously attached is placed in an aquarium and thus can immediately exhibit purification performance.

However, it takes about one week to two months to attach bacteria to the filter for purifying an aquarium as in Japanese Patent Application Laid-Open No. 2005-117925 and it is necessary to store the filter as immersed in an ammonium liquid. Further, pores of the filter are easily clogged as the filter is continuously used, and thus it is necessary to clean and exchange the filter periodically. Nitrifying bacteria attached to the filter are also removed together, and it takes a long time to attach nitrifying bacteria again. Therefore, the problem is that the filter cannot be immediately put in an aquarium and used when necessary.

Further, a filter to which bacteria are attached is generally unnoticeably placed in an ornamental aquarium on purpose, since the filter causes deterioration in the beauty.

The present invention has been achieved in view of such circumstances. An object of the present invention is to provide entrapping immobilization pellets which can exhibit purification performance immediately after being placed in an aquarium and furthermore can provide a color, luster, and the like for the main body or periphery of the aquarium to improve the beauty of the whole aquarium environment; a process and an apparatus for purifying breeding water; and an aquarium set.

SUMMARY OF THE INVENTION

According to a first aspect of the present invention, to attain the aforementioned object, there is provided entrapping immobilization pellets for purifying breeding water in an aquarium to breed aquatic animals, wherein microorganisms are entrapped and immobilized in an aqueous polymer gel and the entrapping immobilization pellets are colored.

According to the first aspect, since microorganisms to purify breeding water are previously immobilized in the entrapping immobilization pellets, the pellets can purify breeding water immediately after being placed in an aquarium. Further, since the entrapping immobilization pellets are colored, a color or luster can be provided for an aquarium and its periphery and the beauty can be improved.

The entrapping immobilization pellets may be colored by a process of previously mixing a colorant such as a dye or a pigment prior to forming a gel, for example. Examples of the colorant include lustrous pigments and powders (such as lame and pearl).

According to a second aspect of the present invention, to attain the aforementioned object, there is provided entrapping immobilization pellets for purifying breeding water in an aquarium to breed aquatic animals, wherein the entrapping immobilization pellets have a phosphorus content of 0.05 mass % or less.

According to a third aspect of the present invention, to attain the aforementioned object, there is provided entrapping immobilization pellets for purifying breeding water in an aquarium to breed aquatic animals, wherein the entrapping immobilization pellets contain an algaecide.

According to the second and third aspects, algae can be prevented from being generated in and attached to the inside of an aquarium and the entrapping immobilization pellets, and the beauty of the whole aquarium can be improved.

According to a fourth aspect of the present invention, to attain the aforementioned object, there is provided entrapping immobilization pellets for purifying breeding water in an aquarium to breed aquatic animals, wherein the entrapping immobilization pellets contain a pH indicator.

According to the fourth aspect, the entrapping immobilization pellets can visually display a pH change in an aquarium by a subtle color change in the pH indicator. Thus, the beauty of the whole aquarium can be improved and the time for exchanging water can be informed.

According to a fifth aspect of the present invention, there is provided the entrapping immobilization pellets for purifying breeding water according to any one of the first to fourth aspects, wherein the microorganisms contained in the entrapping immobilization pellets are nitrifying bacteria.

According to the fifth aspect, nitrifying bacteria can remove ammonium nitrogen or nitrite nitrogen in breeding water.

According to a sixth aspect of the present invention, to attain the aforementioned object, there is provided a process for purifying breeding water in an aquarium to breed aquatic animals, the process comprising: bringing the breeding water to breed aquatic animals into contact with the entrapping immobilization pellets according to any one of the first to fifth aspects to purify the breeding water.

According to the sixth aspect, the entrapping immobilization pellets can exhibit purification performance immediately after being placed in an aquarium and furthermore can improve the beauty of the inside or periphery of the aquarium by various colors and a color change.

According to a seventh aspect of the present invention, to attain the aforementioned object, there is provided an apparatus for purifying breeding water in an aquarium to breed aquatic animals, the apparatus comprising: a transparent purification tank having an intake port to take in breeding water in the aquarium and a return port to return the purified breeding water into the aquarium; the entrapping immobilization pellets according to any one of the first to fifth aspects provided in the purification tank; and an air supply device to supply air into the purification tank.

According to an eighth aspect of the present invention, there is provided the apparatus for purifying breeding water according to the seventh aspect, wherein aquarium lighting is provided in the purification tank.

According to the seventh and eighth aspects, when the apparatus is merely placed inside or outside an existing aquarium, breeding water can be purified and the beauty of the whole aquarium can be improved. The purification tank of the seventh aspect includes a purification tank having a port used as both the intake port and the return port.

According to a ninth aspect of the present invention, to attain the aforementioned object, there is provided an aquarium set comprising: the purification apparatus according to the seventh or eighth aspect placed in an aquarium to breed aquatic animals.

According to a tenth aspect of the present invention, to attain the aforementioned object, there is provided an aquarium set comprising: an aquarium to breed aquatic animals; the purification apparatus according to the seventh or eighth aspect placed outside the aquarium; an intake pipe that makes the inside of the aquarium communicate with the intake port of the purification apparatus to take in the purification apparatus breeding water in the aquarium; a return pipe that makes the return port of the purification apparatus communicate with the inside of the aquarium to return into the aquarium the breeding water purified in the purification apparatus; and a circulation device to circulate the breeding water between the aquarium and the purification apparatus.

According to an eleventh aspect of the present invention, to attain the aforementioned object, there is provided an aquarium set comprising: the entrapping immobilization pellets according to any one of the first to fifth aspects in an aquarium to breed aquatic animals.

The entrapping immobilization pellets of the present invention can exhibit purification performance immediately after being placed in an aquarium and furthermore can provide a color, luster, and the like for the main body or periphery of the aquarium to improve the beauty of the whole aquarium environment.

DETAILED DESCRIPTION OF THE PREFERRED EMBODIMENTS

First, a process for producing the entrapping immobilization pellets of the present invention will be described.

Figure 1:
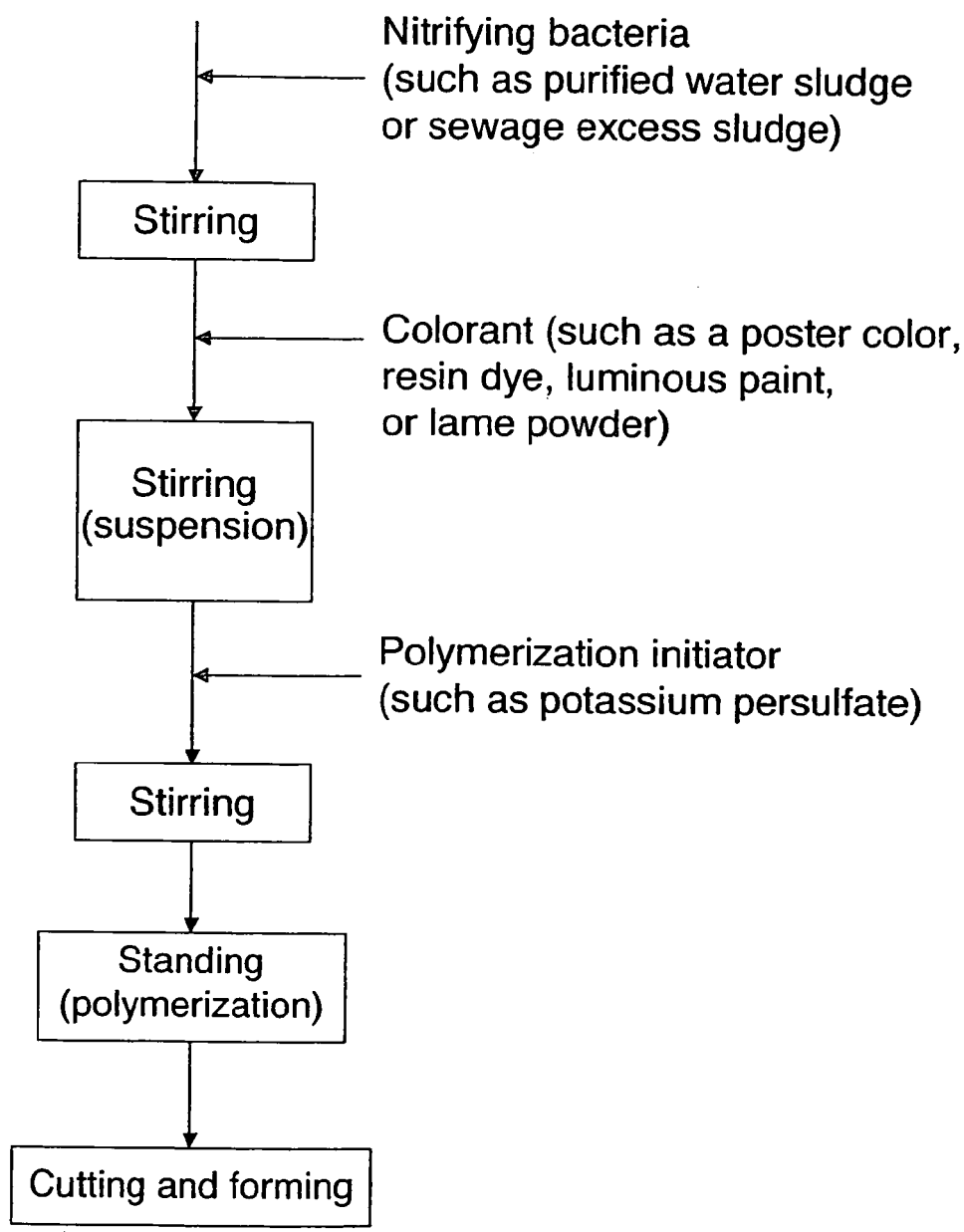
FIG. 1 is a flow chart showing an example of a process for producing the entrapping immobilization pellets of the present invention.

FIG. 1 is a flow chart showing an example of the process for producing the entrapping immobilization pellets of the present invention.

As shown in FIG. 1, a polyethylene glycol prepolymer (hereinafter referred to as PEG) as an immobilizing material is first mixed with N,N,N',N'-tetramethylethylenediamine as a polymerization accelerator to prepare a mixed solution, and the pH of the mixed solution is adjusted to around the neutrality (6.5 to 8.5) to prepare a gel raw material solution.

Next, the gel raw material solution is mixed with purified water sludge and the mixture was stirred, and subsequently a poster color is further added as a colorant and the mixture was stirred to prepare a suspension.

Next, potassium persulfate as a polymerization initiator is added to the suspension, and the mixture was stirred and then immediately gelled (polymerized) into a sheet or a block. Here, gelation is carried out at a polymerization temperature of 15 to 40° C., and preferably 20 to 30° C., for a polymerization time of 5 to 60 minutes, and preferably 10 to 60 minutes.

The gelled sheet is punched into a predetermined shape by a punching die modeled in the shape of a heart, star, moon, petal, human being, cloud, etc., so that the entrapping immobilization pellets of the present invention are formed.

The size of each entrapping immobilization pellet is not specifically limited, but is preferably 1 mm to 5 mm square, and more preferably about 3 mm square. Thus, entrapping immobilization pellets can be obtained having nitrifying bacteria immobilized in an aqueous polymer gel colored with various colors such as wine red, transparent green, and fluorescent yellow.

FIG. 1 describes a process in which purified water sludge is added to a gel raw material solution and then a colorant is added; however, the order of addition is not limited thereto. It is also possible to add a colorant to a gel raw material solution and then add purified water sludge. The shape of the entrapping immobilization pellets is not limited to the aforementioned shape, and the pellets may be formed by cutting into common 3 mm-square substantial cubes, cylinders, or balls. The entrapping immobilization pellets may be produced not only by the aforementioned sheet forming, but also by tube forming, drop granulation, block forming, or the like.

The colorant used in the present invention is not specifically limited insofar as it is colorable; examples of the colorant include a dye, a pigment, a luminous paint, a poster color, and a gouache. Further examples of the colorant include powders having metallic luster (such as lame powder and pearl powder). Lame powder generally refers to a powder obtained from a polyester film colored with a metallic color by vacuum deposition of a metal and coated with a dye-containing or colorless resin on the deposition surface and the back surface.

Known dyes having various colors may be used as the dye. Examples of the dye include direct dyes, acid dyes, food dyes, basic dyes, reactive dyes, dispersed dyes, luminous paints, and fluorescent dyes.

Known pigments having various colors may be used as the pigment. Specific examples of the pigment include inorganic pigments such as carbon blacks such as acetylene black, channel black, and furnace black, in particular, self-dispersible carbon black whose surface is modified by various hydrophilic groups when dispersed in an aqueous phase, metallic powders such as aluminum powder and bronze powder, iron red, chrome yellow, ultramarine blue, chromic oxide, and titanium oxide; organic pigments such as phthalocyanine pigments such as metal-free phthalocyanine pigments and copper phthalocyanine pigments, azo pigments such as insoluble azo pigments, azo lake pigments, condensed azo pigments, and chelate azo pigments, condensed polycyclic pigments such as anthraquinone pigments, quinacridone pigments, isoindolinone pigments, isoindoline pigments, dioxazine pigments, threne pigments, perylene pigments, perynone pigments, thioindigo pigments, quinophthalone pigments, and metal complex pigments, and lake pigments of acid or basic dyes; and fluorescent pigments. Fluorescent pigments include so-called synthetic resin solid solution-type fluorescent pigments obtained by performing bulk polymerization of a synthetic resin, dissolving or dyeing a fluorescent pigment developing various hues during or after the polymerization, and finely crushing the resulting colored bulk resin. Fluorescent pigments also include melamine resins, urea resins, sulfonamide resins, alkyd resins, and polyvinyl chloride resins on which a pigment is supported.

The amount of the colorant added is enough if the entrapping immobilization pellets can be colored and strength of the aqueous gel can be ensured, and such an amount is preferably 0.04 to 5 mass % based on the pellets.

Suitable examples of the microorganisms to be entrapped and immobilized include nitrifying bacteria or complex microorganisms comprising nitrifying bacteria, denitrifying bacteria, and anaerobic ammonium oxidizing bacteria for the purpose of removing nitrogen; and microorganisms that can decompose specific toxic chemical substances such as dioxins (pure microorganisms such as water bloom decomposing bacteria, PCB decomposing bacteria, dioxin decomposing bacteria, and environmental hormone decomposing bacteria, for example). The microorganisms refer not only to microorganisms concentrated and separated by culturing or the like, but also to substances containing various microorganisms such as activated sludge in sewage treatment plants, sludge in lakes, rivers, or sea, and soil. In the present embodiment, it is preferable to use purified water sludge containing only a small amount of phosphorus that is a cause of generation of algae in an aquarium. Dewatered sludge, concentrated sludge, or sun-dried sludge may be used as such microorganism-containing sludge. The phosphorus content in each entrapping immobilization pellet is preferably 0.05 mass % or less.

Examples of the immobilizing material include a monomer, a prepolymer, and an oligomer, but the immobilizing material is not specifically limited. For example, polyacrylamide, polyvinyl alcohol, polyethylene glycol, sodium alginate, carageenan, or agar can be used. Examples of the immobilizing agent prepolymer that can be used include the following compounds:

monomethacrylates such as polyethylene glycol monomethacrylate, polyprene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate;

monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobomyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;

dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane;

trimethacrylates such as trimethylolpropane trimethacrylate;

triacrylates such as trimethylolpropane triacrylate, pentaerythritol triacrylate, trimethylolpropane EO-added triacrylate, glycerol PO-added triacrylate, and ethoxylated trimethylolpropane triacrylate;

tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate; and
other prepolymers such as acrylamide, acrylic acid, and dimethylacrylamide.

The immobilizing materials may be used singly or in a combination of two or more.

Polymerization of the entrapping immobilization pellets is most appropriately radical polymerization using potassium persulfate, but may be polymerization using ultraviolet rays or electron beams or redox polymerization. In polymerization using potassium persulfate, it is preferable to add 0.001 to 0.25 mass % of potassium persulfate and 0.01 to 0.5 mass % of an amine polymerization accelerator. As the amine polymerization accelerator, β-dimethylaminopropionitrile, N,N, N', N'- tetramethylethylenediamine, or the like may be preferably used.

An indicator involving a color change such as a pH indicator may be used as the colorant. The pH indicator may be any pH indicator that has a transition interval around the neutral pH. For example, methyl red (transition interval: pH 4.4 to 6.2), bromothymol blue (transition interval: pH 6.0 to 7.6, also called BTB reagent), or cresol red (transition interval: pH 7.2 to 8.8) may be suitably used. However, bromothymol blue is preferably used, since the pH indicator is changed in color when pH in the pellets is too much alkaline or acidic and thus may adversely affect the living environment of microorganisms in the pellets. As the pH indicator, BTB powder, fine powder obtained by crushing pH test paper, or the like may be used. The amount of the pH indicator added is preferably 0.01 to 2 mass % based on the entrapping immobilization pellets.

In the entrapping immobilization pellets in which nitrifying bacteria are entrapped and immobilized in this manner, nitrification reaction of $NH_4^+ + 2O_2 \rightarrow NO_3^- + H_2O + 2H^+$ occurs and hydrogen ions are generated, so that pH is reduced. Accordingly, the pH of the entrapping immobilization pellets is turned to be acidic and the pH indicator contained in the pellets is changed in color, and thus appearance of the pellets themselves is changed in color. In this case, when nitrifying bacteria in the entrapping immobilization pellets show insufficient activity and nitrification reaction does not proceed, the pH indicator is not changed in color and thus appearance of the pellets themselves is not changed in color. Therefore, activity of nitrifying bacteria in the entrapping immobilization pellets can be visually determined immediately, and the time for exchanging the entrapping immobilization pellets or water can be informed.

The entrapping immobilization pellets of the present invention may also contain an algaecide in order to maintain the beauty of the entrapping immobilization pellets. A conventional algaecide may be used as such an algaecide. The amount of the algaecide is enough if bred aquatic animals are not adversely affected and the entrapping immobilization pellets can be produced with practical strength, and such an amount is preferably 0.01 to 3 mass % based on the entrapping immobilization pellets. When the algaecide is added in this manner, algae can be prevented from being grown in and attached to the inside of an aquarium and the entrapping immobilization pellets.

The entrapping immobilization pellets formed into various shapes may also contain a combination of two or more of the algaecides, pH indicators, and colorants as described above.

The entrapping immobilization pellets of the present invention can be obtained with different gravities by controlling the content or size of a material forming the entrapping immobilization pellets. This can make the entrapping immobilization pellets floated in water in various forms.

Aquatic animals are not specifically limited and include all animals living in water such as freshwater fish such as neon tetra, goldfish, and killifish; saltwater fish such as horse mackerel and porgy; shellfish such as crab and shrimp; and jellyfish.

Two or more types of the entrapping immobilization pellets having different colors, shapes, compositions, gravities, and the like may be used in combination.

Next, there will be described a process and an apparatus for purifying breeding water and an aquarium set using the entrapping immobilization pellets of the present invention produced as described above.

First Embodiment

First, a configuration of an aquarium set 10 of the present embodiment will be described.

Figure 2:
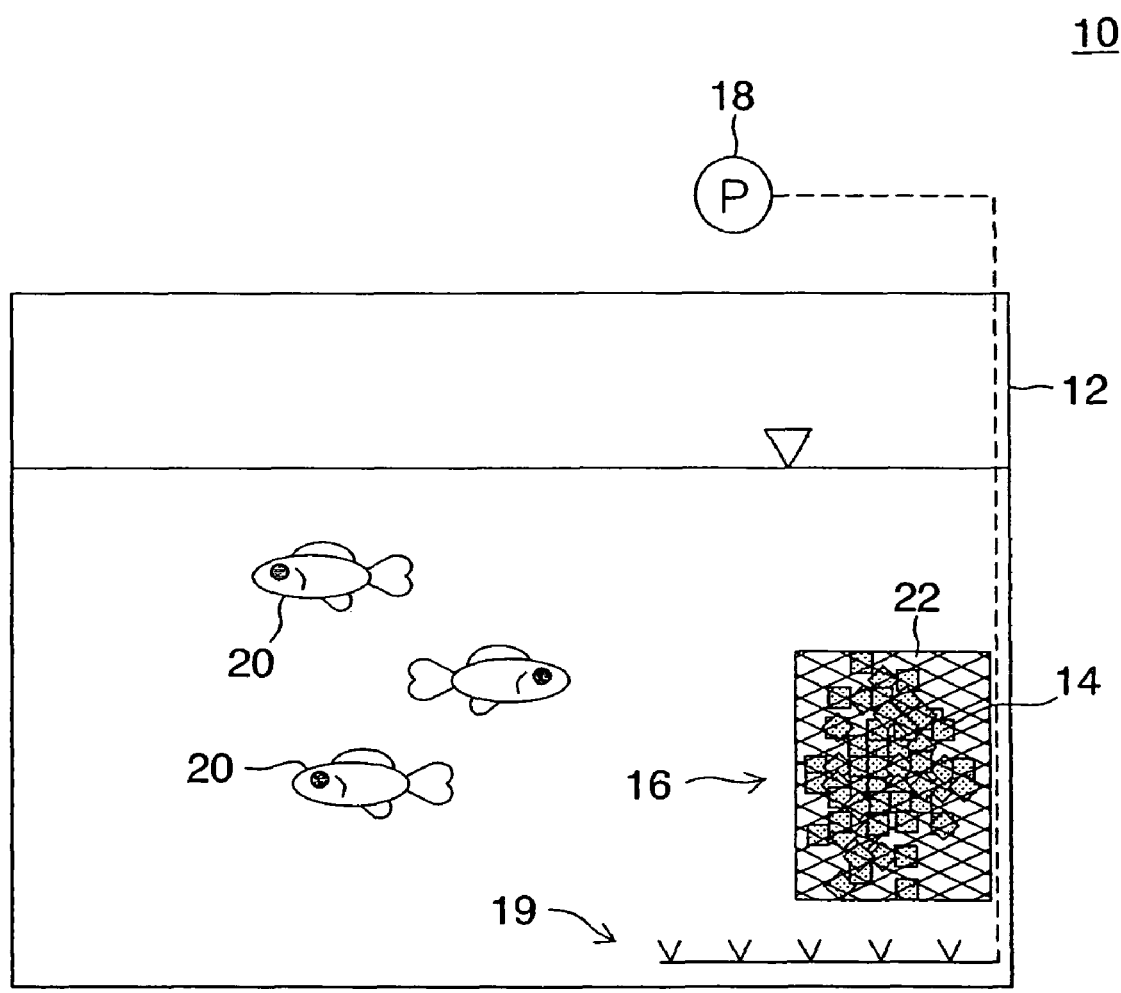
FIG. 2 is a view describing a configuration of an aquarium set of a first embodiment.

FIG. 2 is a view describing a configuration of the aquarium set 10 of the present embodiment. The present embodiment is an example in which a purification material or a simple purification apparatus having the entrapping immobilization pellets colored is placed in an aquarium.

As shown in FIG. 2, the aquarium set 10 comprises, as main components, an aquarium 12 to breed aquatic animals; and a purification material 16 internally having the entrapping immobilization pellets 14 of the present invention to purify breeding water in the aquarium 12.

The aquarium 12 is a transparent aquarium made of glass or plastic, and a diffuser pipe 19 communicating with an air pump 18 is provided in the aquarium 12. The aquarium 12 is filled with breeding water, and aquatic animals such as ornamental fish are bred in the aquarium 12.

The entrapping immobilization pellets 14 covered with a protection net 22 such as a network-shaped one can be suitably used as the purification material 16. Thus, the entrapping immobilization pellets 14 can be prevented from being eroded by aquatic animals.

The amount of the entrapping immobilization pellets 14 introduced into the aquarium 12 is set to realize a preferable nitrification speed. In the present invention, the nitrification speed is preferably set to be about 30 to 40 times the speed of generating ammonium by bred aquatic animals.

Next, the action of the aquarium set 10 of the present embodiment will be described.

First, the entrapping immobilization pellets 14 covered with the protection net 22 are introduced into the aquarium 12. This brings the entrapping immobilization pellets 14 in the protection net 22 into contact with breeding water.

Nitrifying bacteria or the like in the entrapping immobilization pellets 14 decompose and remove ammonium nitrogen in breeding water to purify the breeding water.

The entrapping immobilization pellets 14 colored with a brilliant color as described above can provide a color for the aquarium. The entrapping immobilization pellets dyed with a dye not impairing transparence, a fluorescent paint, a luminous paint, lame powder having metallic luster, or the like glow with natural light or light from lighting placed in the aquarium and can provide a color or luster for the aquarium. Further, the entrapping immobilization pellets dyed with a luminous paint slightly glow even in the dark, and thus can create a fantastic mood. The colored entrapping immobilization pellets are floated in the protection net 22 by air from the diffuser pipe 19, so that the beauty can be further improved. Accordingly, breeding water can be purified immediately after introduction of the entrapping immobilization pellets, and furthermore the beauty of the aquarium can be further improved.

The present embodiment is described taking an example in which the entrapping immobilization pellets 14 covered with the protection net 22 are placed in the aquarium 12 as the purification material 16; however, the present embodiment is not limited to this example and the pellets can have various forms.

Figure 3:
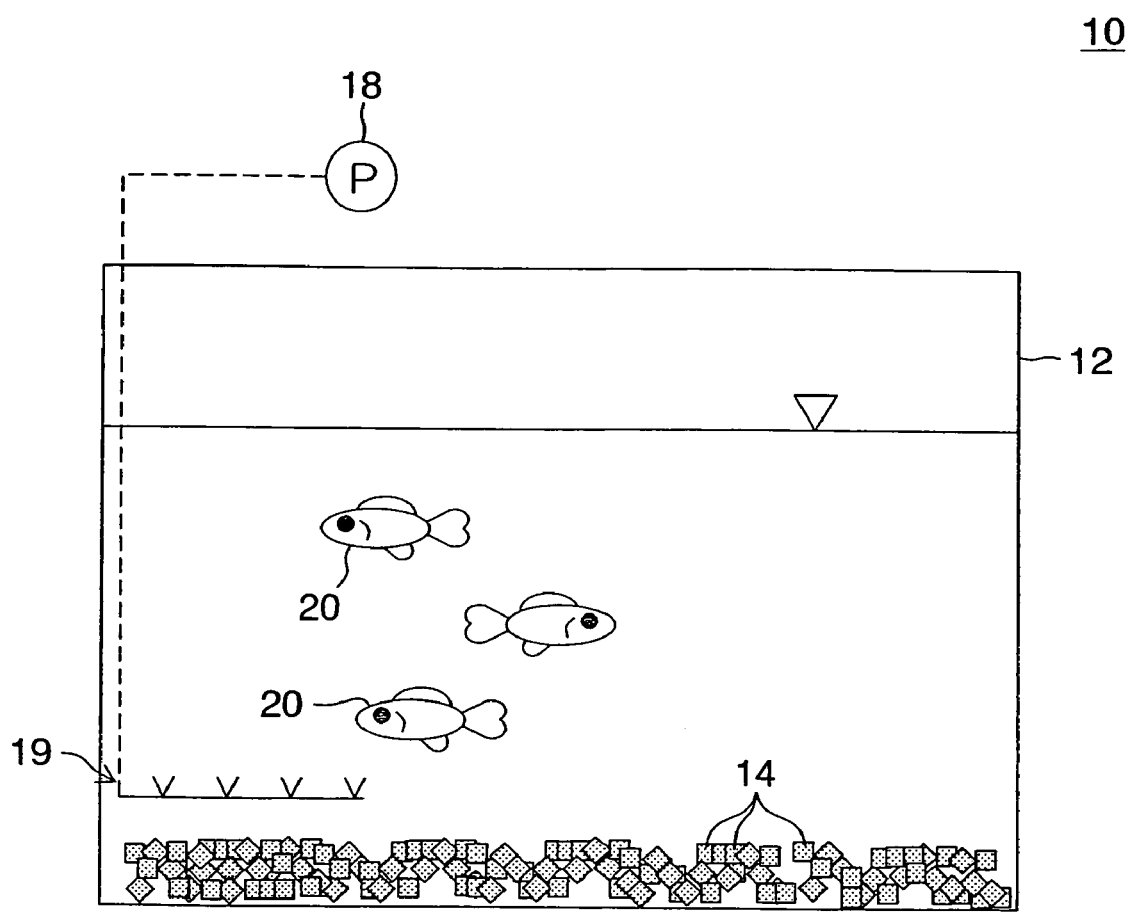
FIG. 3 is a view describing a modification of FIG. 2.

FIG. 3 is a view describing a configuration of an aquarium set 10' which is a modification of FIG. 2 and comprises the entrapping immobilization pellets 14 of the present invention directly paved as paving sand on the bottom of an aquarium 12.

In the example of FIG. 3, when using the entrapping immobilization pellets 14 formed into various shapes by controlling the gravity, contact efficiency with breeding water can be improved and furthermore the pellets can be arranged more variously. For example, the entrapping immobilization pellets may not only be formed into paving sand in the aquarium 12 but also be formed into petals and allowed to hover in the aquarium.

Figure 4:
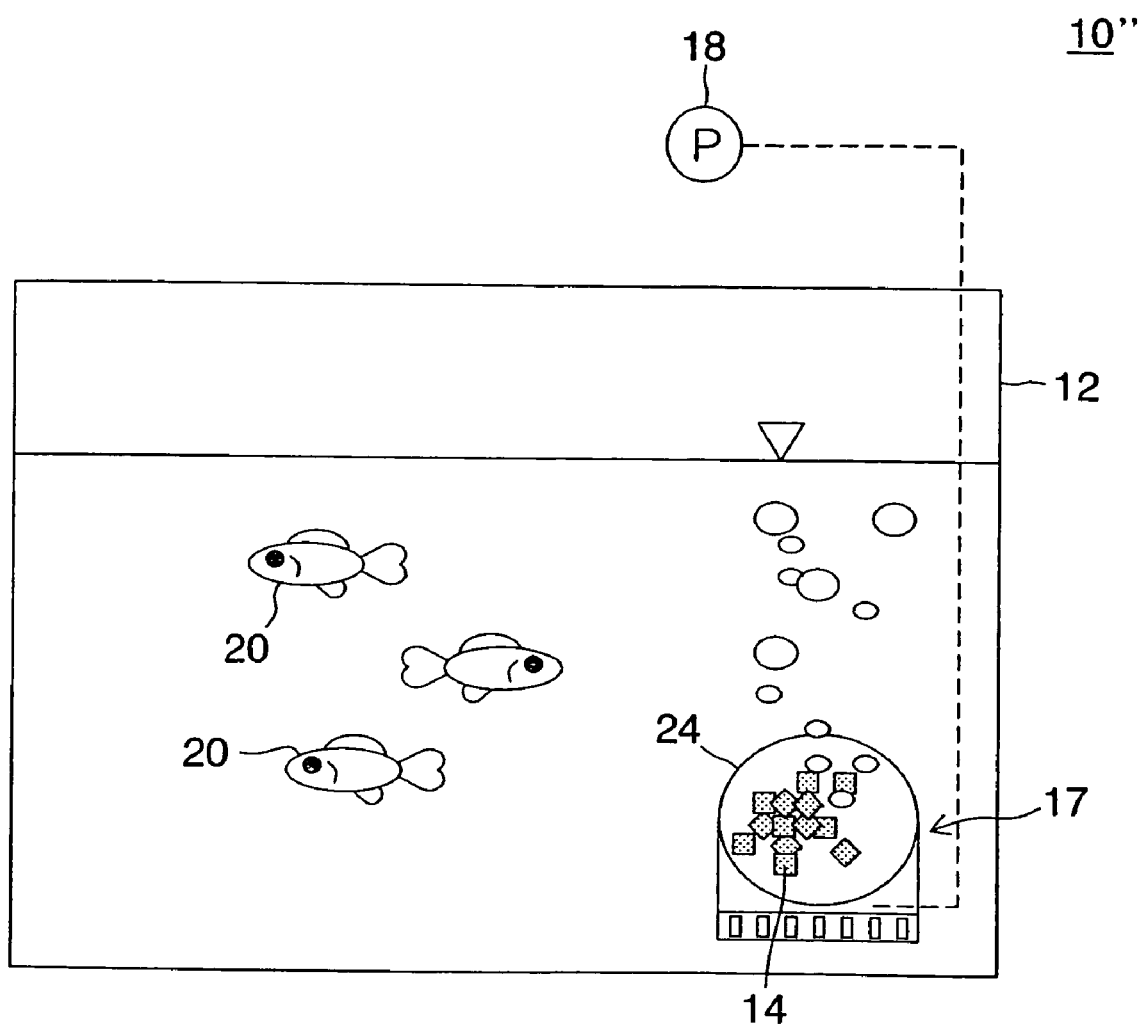
FIG. 4 is a view describing a modification of FIG. 2.

FIG. 4 is a view describing a configuration of an aquarium set 10" which is a modification of FIG. 2 and comprises a simple purification apparatus 17 having the entrapping immobilization pellets 14 of the present invention included in a transparent rotation drum.

Figure 5:
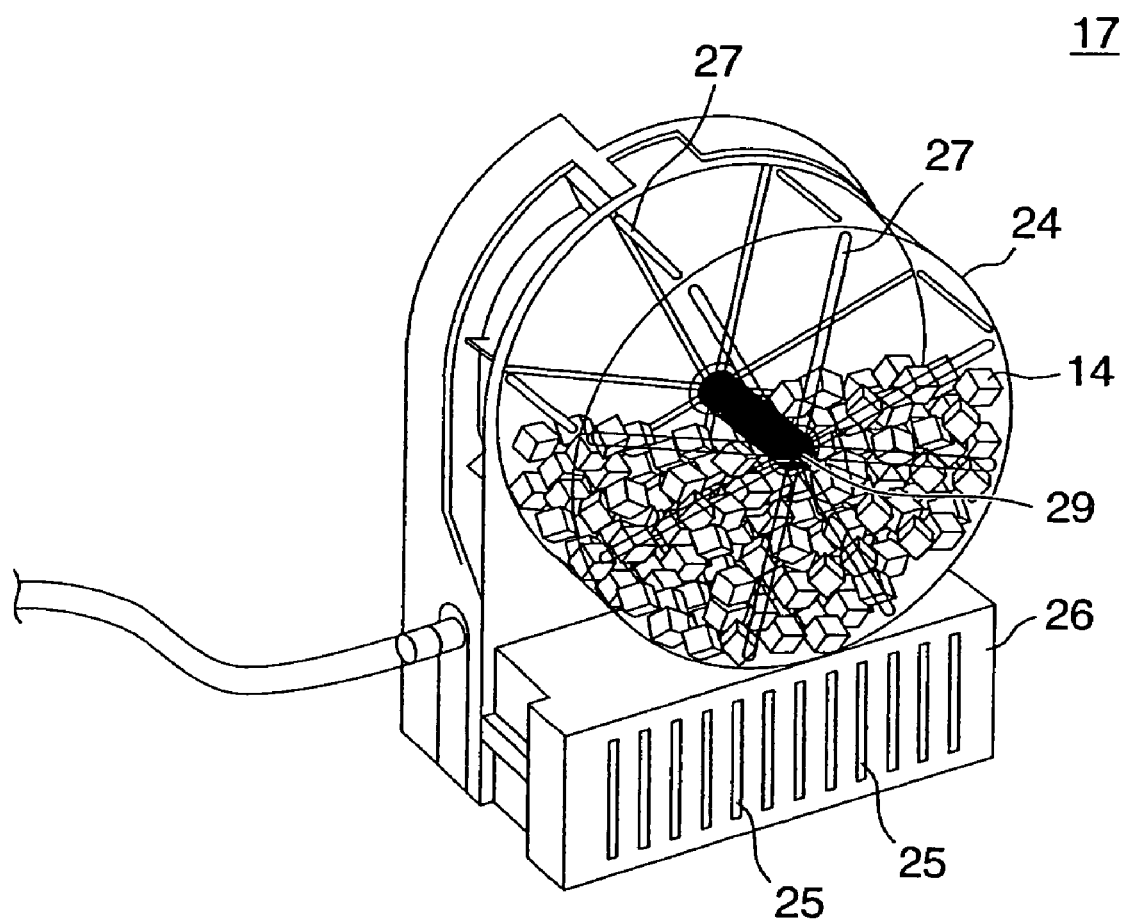
FIG. 5 is an oblique view describing a configuration of a simple purification apparatus of FIG. 4.

FIG. 5 is an oblique view showing a configuration of the simple purification apparatus 17.

As shown in FIG. 5, in the simple purification apparatus 17, the transparent rotation drum 24 in which the entrapping immobilization pellets 14 are included is supported by a support 26 having on the side surface a plurality of slit holes 25 in which breeding water is taken.

The rotation drum 24 can be rotated by a flow of air supplied from an air pump 18 with a drum axis 29 in the center. A plurality of slit holes 27 are provided in the periphery of the rotation drum 24. Filter media can be stored in the support 26 which can thus also function as a filter tank.

As such a simple purification apparatus 17, a commercially available product may be used, and Bacter Cel System Rotor (trade name, manufactured by GEX) or Rotor Boy (trade name, manufactured by GEX) may be preferably used, for example.

In such a configuration, air is supplied into the rotation drum 24 by the air pump 18, and the rotation drum 24 starts to be rotated by an air flow. Accordingly, breeding water is taken in the rotation drum 24 through the plurality of slit holes 25 provided in the support 26.

After being brought into contact with the entrapping immobilization pellets 14 and purified in the rotation drum 24, the breeding water is discharged from the plurality of slit holes 27 on the surface of the rotation drum 24 and returned to the aquarium 12.

Accordingly, the aforementioned effect can be exhibited, and furthermore a color or motion of light of the colored entrapping immobilization pellets 14 flowing in the rotation drum 24 can be watched and enjoyed. Purified breeding water can be homogeneously stirred in the aquarium 12 by rotation of the rotation drum 24.

FIG. 4 describes an example in which the simple purification apparatus using the rotation drum 24 is placed in the aquarium 12; however, it is possible to pack the entrapping immobilization pellets 14 in a transparent spherical container having a plurality of holes formed on the surface and make the container floated in the aquarium 12.

Figure 6A:
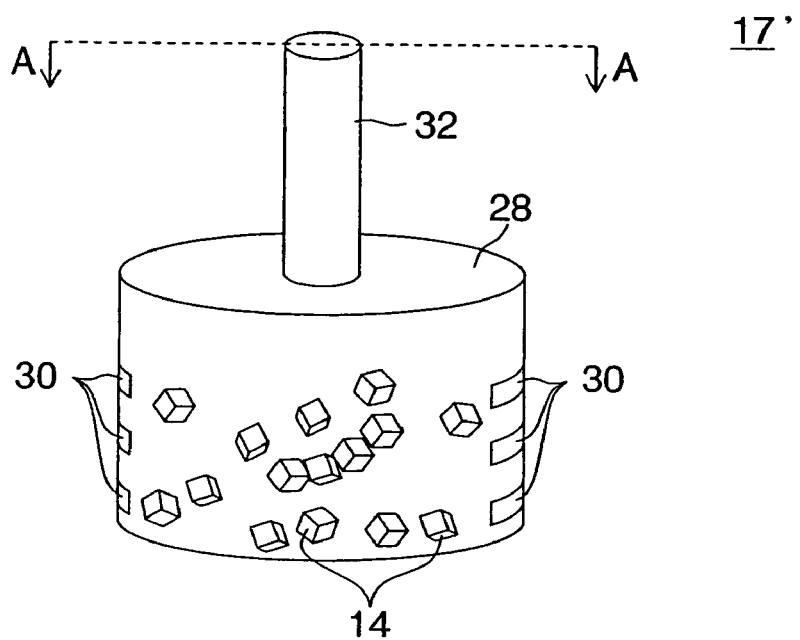
FIGS. 6A and 6B are views describing a modification of the simple purification apparatus of FIG. 4.
Figure 6B:
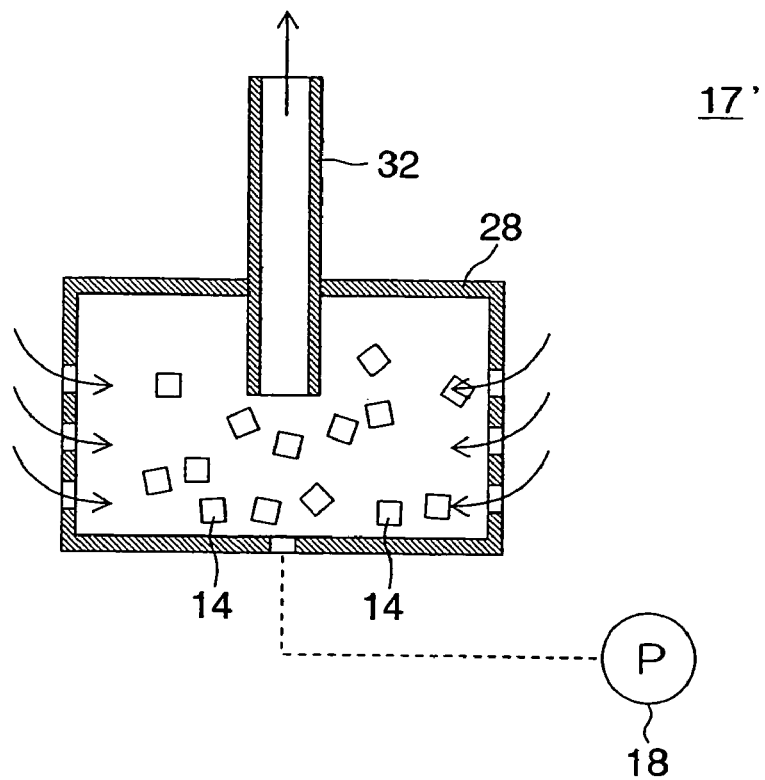

FIGS. 6A and 6B are views describing a modification of the simple purification apparatus 17 of FIG. 4. In FIGS. 6A and 6B, FIG. 6A is an oblique view showing a configuration of a simple purification apparatus 17', and FIG. 6B is an A-A line cross-sectional view of FIG. 6A.

The simple purification apparatus 17' shown in FIGS. 6A and 6B comprises a transparent container 28 in which the entrapping immobilization pellets 14 are packed. An intake port 30 for breeding water is provided on the side surface of the container 28, and a return pipe 32 for breeding water is provided to extend vertically upward from the inside of the container 28. An air intake port 34 of taking air through an air pump 18 is provided on the bottom of the container 28 (see FIG. 6B). The shape of the container 28 is not limited to that of FIGS. 6A and 6B and may be rectangular, for example.

In such a configuration, since an intake port and a return port for breeding water are separately provided, the aforementioned effect of the present embodiment can be exhibited, and furthermore breeding water can be efficiently purified using a circulating water flow from down to up.

The present embodiment shows an example in which the entrapping immobilization pellets are used as colored; however, it is obviously possible to use a combination of two or more types of the entrapping immobilization pellets formed into various shapes, the entrapping immobilization pellets containing an algaecide, the entrapping immobilization pellets containing a pH indicator, and the like. The entrapping immobilization pellets formed into various shapes may also contain at least one of the algaecides, pH indicators, and colorants.

Second Embodiment

First, a configuration of an aquarium set 40 of the present embodiment will be described.

Figure 7:
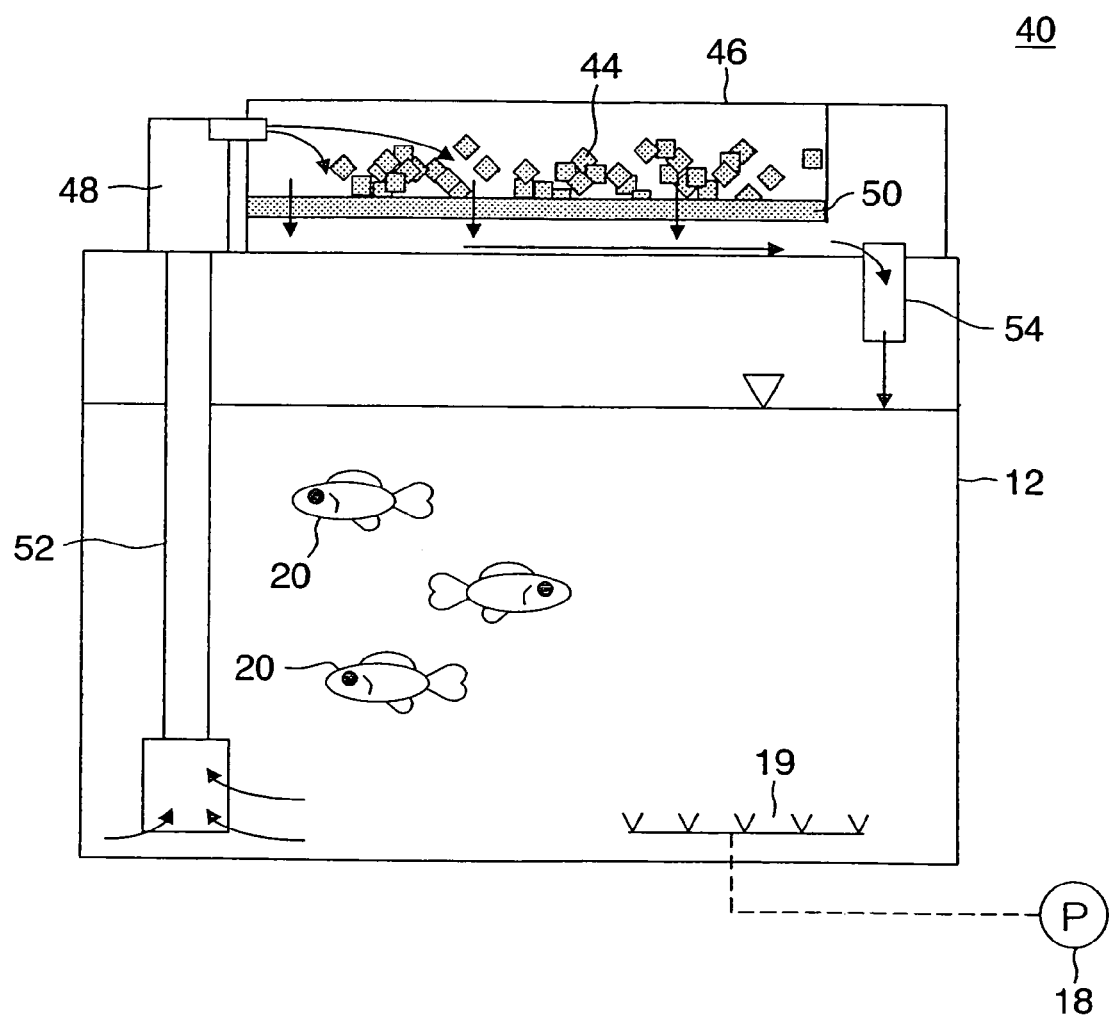
FIG. 7 is a view describing a configuration of an aquarium set of a second embodiment.

FIG. 7 is a view describing a configuration of the aquarium set 40 of the present embodiment. The present embodiment is an example in which a filter unit placed in the main body of an aquarium is used as an apparatus for purifying breeding water. The same members as in the first embodiment and members having the same function as in the members of the first embodiment are indicated by the same symbols, and detailed description of such members is omitted.

As shown in FIG. 7, the aquarium set 40 comprises, as main components, an aquarium 12 to breed aquatic animals; a filter unit 46 internally having the entrapping immobilization pellets 44 of the present invention to purify breeding water in the aquarium 12; and a lifting pump 48 provided in the upper part of the aquarium 12 to supply breeding water to the filter unit 46 from the aquarium 12.

The aquarium 12 is a transparent aquarium made of glass or plastic, and a diffuser pipe 19 is provided in the aquarium 12. The aquarium 12 is filled with breeding water, and aquatic animals such as ornamental fish 20 are bred in the aquarium 12.

The filter unit 46 is a transparent tank (purification tank) made of glass or plastic, and internally has a filter 50 to remove foreign matter or the like contained in breeding water; and the entrapping immobilization pellets 44 of the present invention which are paved on the filter 50 and decompose and remove ammonium nitrogen in breeding water.

An intake port (not shown) to take in breeding water is provided on the upstream side of the filter unit 46 (left side in FIG. 7), and the intake port communicates with the lifting pump 48. A suction pipe 52 vertically extending below the water surface of the aquarium 12 is connected to the lifting pump 48.

A return pipe 54 to collectively return breeding water after purification to the aquarium 12 is connected to the downstream side of the filter unit 46 (right side in FIG. 7).

A conventional filter unit formed of a transparent material may be suitably used as such a filter unit 46.

The aforementioned entrapping immobilization pellets may be used as the entrapping immobilization pellets provided in the filter unit 46.

FIG. 7 describes an example of using the diffuser pipe 19; however, it is also possible to provide an air supply line (not shown) to supply air into the aquarium 12 and the filter unit 46, respectively.

The amount of the entrapping immobilization pellets 44 introduced may be the same as in the first embodiment.

Next, the action of the aquarium set 40 of the present invention will be described.

First, breeding water in the aquarium 12 is taken in the filter unit 46 through the suction pipe 52 and the lifting pump 48.

Next, the breeding water taken in is brought into contact with the entrapping immobilization pellets 44 paved on the filter 50. Here, ammonium nitrogen in the breeding water starts to be decomposed by the action of nitrifying bacteria contained in the entrapping immobilization pellets 44.

The breeding water purified by the entrapping immobilization pellets 44 are added dropwise through the filter 50 and returned to the aquarium 12 through the return pipe 54.

The entrapping immobilization pellets colored with a brilliant color can provide a color for the aquarium. The entrapping immobilization pellets dyed with a dye not impairing transparence, a fluorescent paint, a luminous paint, lame powder having metallic luster, or the like glow with light from aquarium lighting or natural light and can provide a color or luster for the filter unit and/or the whole aquarium. Further, the entrapping immobilization pellets dyed with a luminous paint slightly glow even in the dark and thus can create a fantastic mood. Accordingly, breeding water can be purified immediately after introduction of the entrapping immobilization pellets, and furthermore the beauty of the aquarium can be further improved.

The present embodiment is described taking an example in which the one-stage filter unit 46 is used; however, the present embodiment is not limited to this example and it is possible to use a two-stage filter unit, a multi-stage filter unit, or the like.

Figure 8:
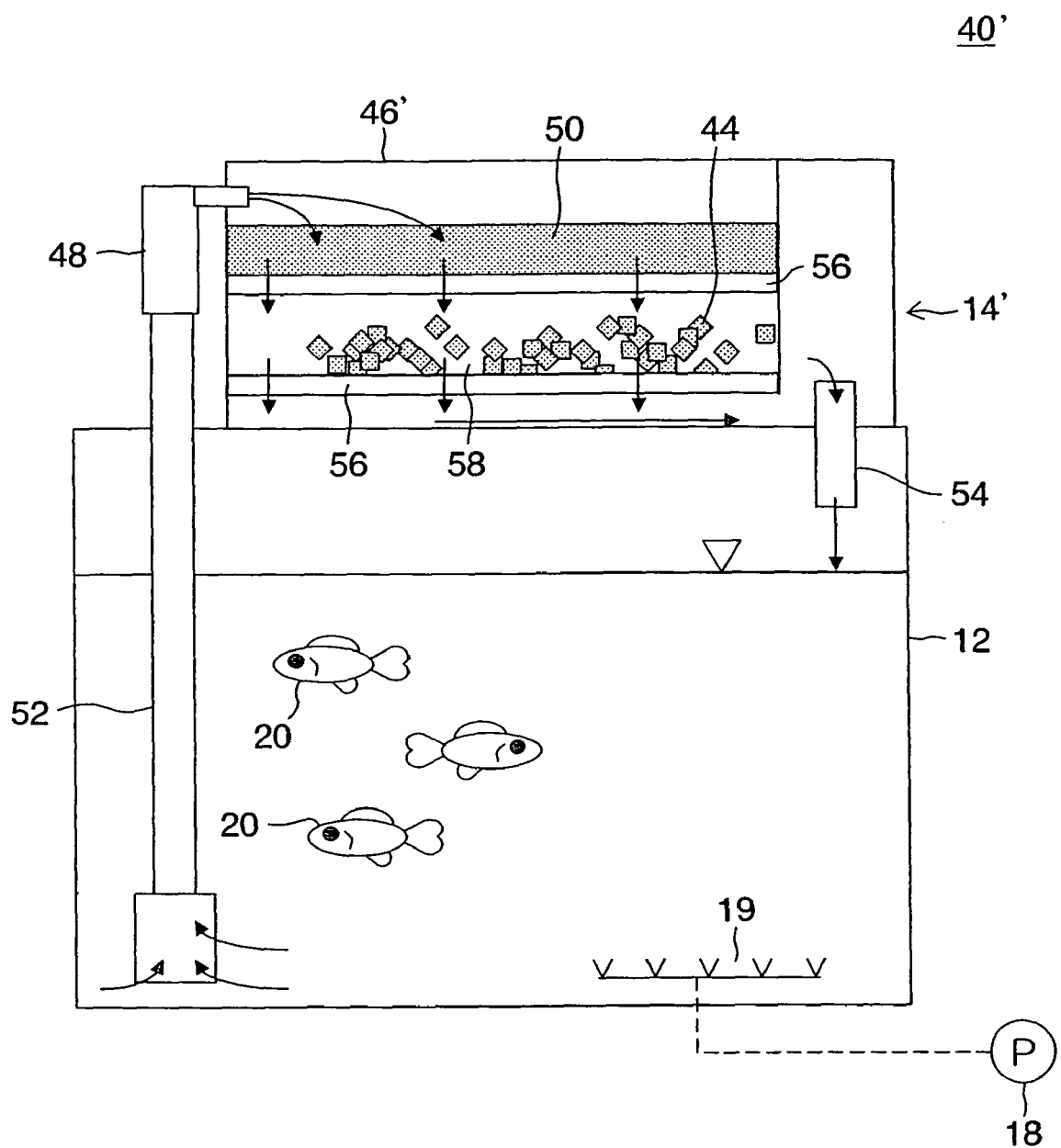
FIG. 8 is a view describing a modification of FIG. 7.

FIG. 8 is a view describing an aquarium set 40' which is a modification of FIG. 7 and comprises a two-stage filter unit 46'.

The two-stage filter unit 46' shown in FIG. 8 internally has two screens 56, 56 opposed to each other; the entrapping immobilization pellets 44 packed in a partitioned part 58 partitioned by the screens; and a filter 50 provided above the partitioned part 58.

In such a configuration, only breeding water from which foreign matter is removed by the filter 50 can be brought into contact with the entrapping immobilization pellets 44. Accordingly, the aforementioned effect can be exhibited, and furthermore foreign matter can be prevented from being attached to the entrapping immobilization pellets 44 and not only purification performance but also the beauty can be improved.

The embodiment of FIG. 7 or 8 is described taking an example in which the filter unit 46 or 46' is placed in the upper part of the aquarium 12; however, the embodiment is not limited to this example, and the filter unit 46 or 46' may be placed on the bottom of the aquarium 12.

Figure 9:
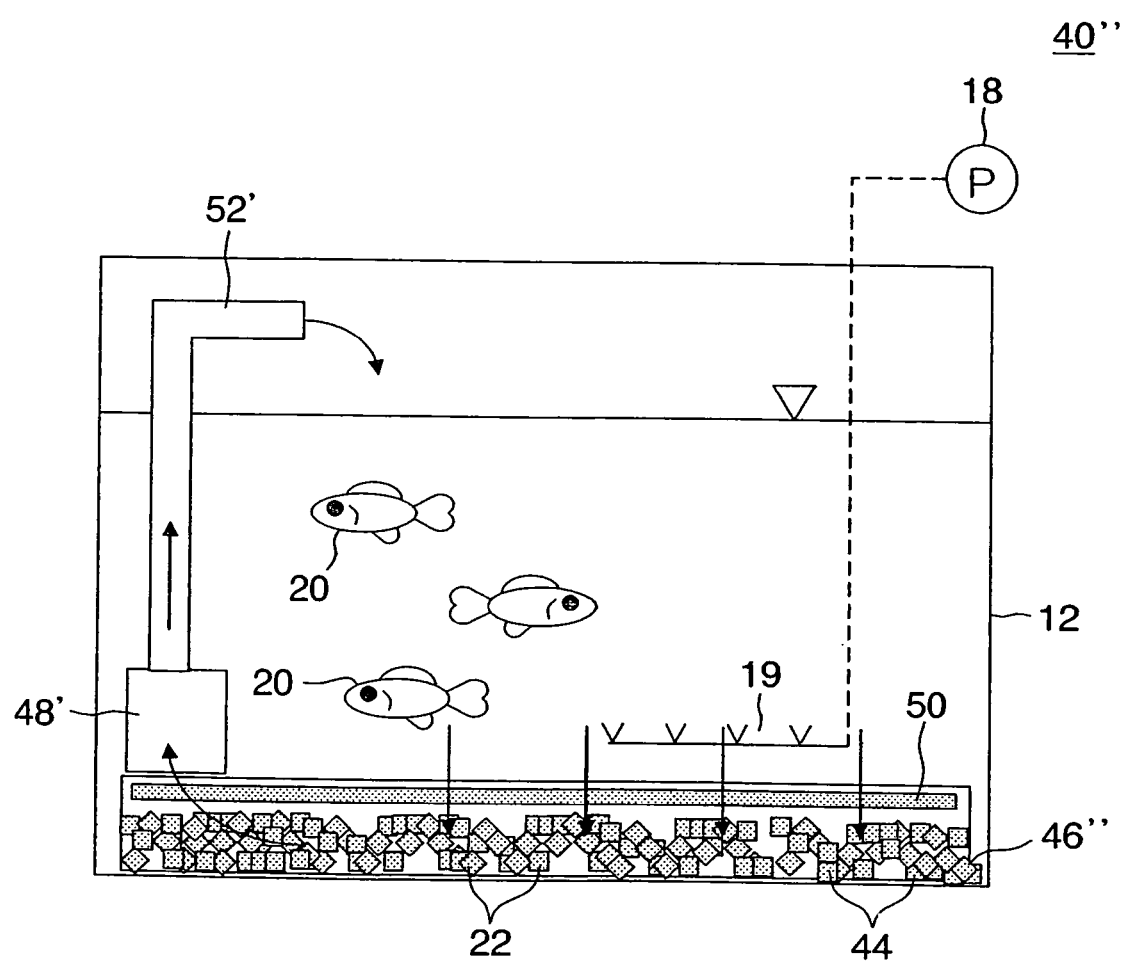
FIG. 9 is a view describing a modification of FIG. 7.

FIG. 9 is a view describing an aquarium set 40" which is a modification of FIG. 7 and in which a filter unit is placed in a different form.

The filter unit 46" of FIG. 9 is placed on the bottom of an aquarium 12. A plurality of holes to take in breeding water (not shown) are formed on the upper surface of the filter unit 46". A filter 50 is provided immediately below the upper surface of the filter unit 46", and the entrapping immobilization pellets 44 are paved below the filter.

In FIG. 9, a lifting pump 48' is placed near the upper surface of the filter unit 46" in the aquarium 12 and communicates with a suction pipe 52'. By the action of the lifting pump 48', breeding water can be taken in the filter unit 46" through the holes formed on the upper surface, and the breeding water after being brought into contact with the entrapping immobilization pellets 44 can be returned to the aquarium 12 from the suction pipe 52'.

In such a configuration, the aforementioned effect of the present embodiment can be exhibited, and furthermore breeding water can be purified without increasing the whole aquarium set in size.

Figure 10:
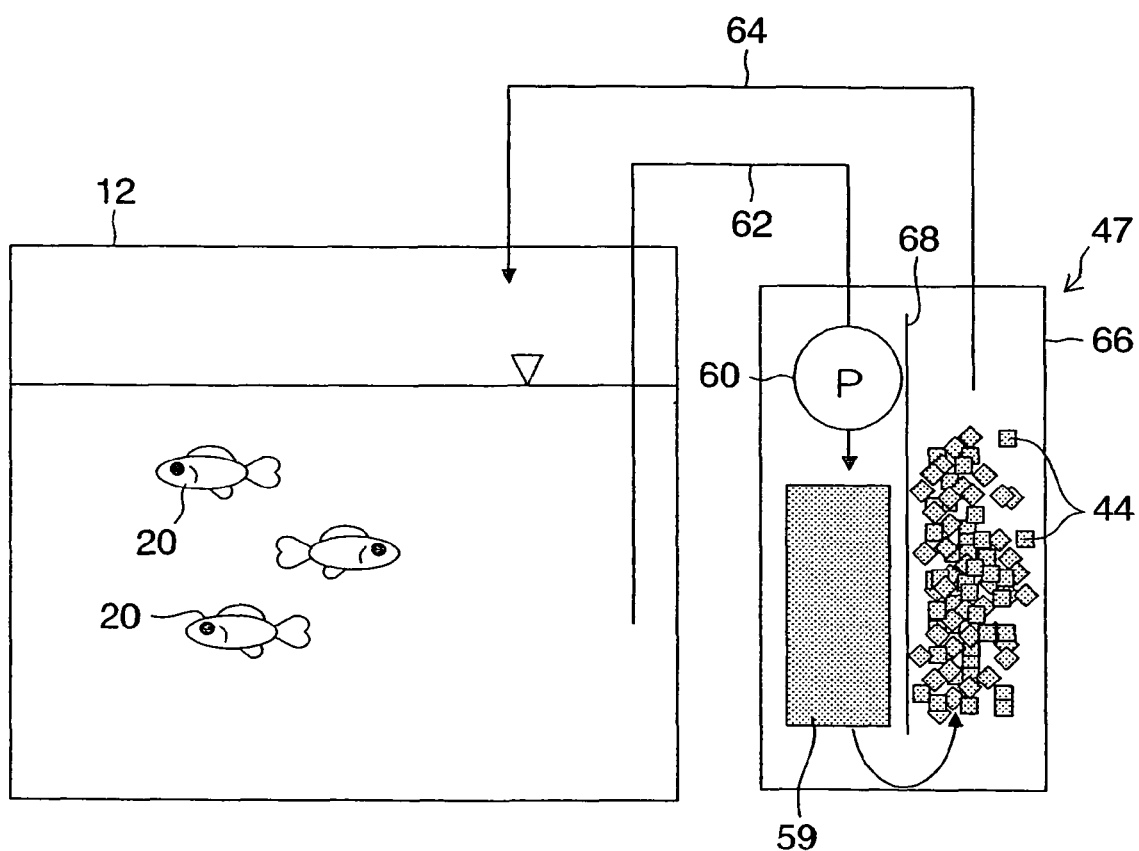
FIG. 10 is a view describing a modification of FIG. 7.

FIG. 10 is a view describing an aquarium set 41 which is a modification of FIG. 7 and in which a filter unit 47 is placed in a different form.

As shown in FIG. 10, the aquarium set 41 comprises, as main components, an aquarium 12; the external filter unit 47 internally having a filter/filter media part 59 and a circulation pump 60 (circulation device); an intake pipe 62 to make the inside of the aquarium 12 communicate with an intake port (not shown) of the external filter unit 47; and a return pipe 64 to make a return port (not shown) of the external filter unit 47 communicate with the inside of the aquarium 12.

The external filter unit 47 is formed by a cylindrical container 66 whose inside is partially partitioned by a partition plate 68. In the external filter unit 47, the circulation pump 60 and the filter/filter media part 59 are stored in one space, and the entrapping immobilization pellets 44 of the present invention are packed in the other space.

The intake pipe 62 extended from the inside of the aquarium is connected to the intake port (not shown) of the external filter unit 47. On the other hand, the return pipe 64 extended to the aquarium is connected to the return port (not shown) of the external filter unit 47.

In such a configuration, the aforementioned effect of the present embodiment can be exhibited, and furthermore the purification apparatus itself can be used as an ornamental.

The present embodiment shows an example in which the entrapping immobilization pellets are used as colored; however, it is obviously possible to use a combination of two or more types of the entrapping immobilization pellets formed into various shapes, the entrapping immobilization pellets containing an algaecide, the entrapping immobilization pellets containing a pH indicator, and the like. The entrapping immobilization pellets formed into various shapes may also contain at least one of the algaecides, pH indicators, and colorants.

Third Embodiment

First, a configuration of an aquarium set 70 of the present embodiment will be described.

Figure 11:
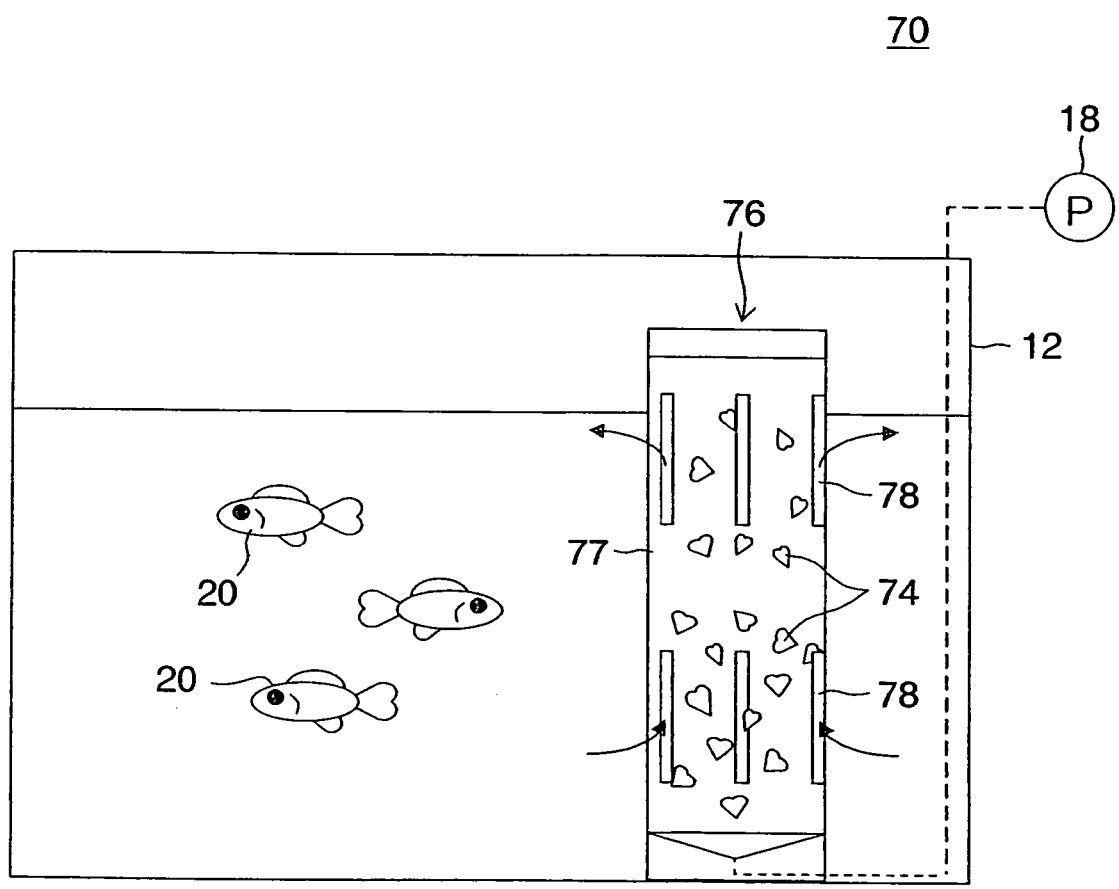
FIG. 11 is a view describing a configuration of an aquarium set of a third embodiment.

FIG. 11 is a view describing a configuration of the aquarium set 70 of the present embodiment. The present embodiment is an example of using, as an apparatus for purifying breeding water, a pellet flotation cylinder in which the colored entrapping immobilization pellets each modeled in the shape of a star, moon, heart, etc. are floated. The same members as in the first embodiment and members having the same function as in the members of the first embodiment are indicated by the same symbols, and detailed description of such members is omitted.

As shown in FIG. 11, the aquarium set 70 is formed almost in the same manner as in the second embodiment, except that the aquarium set 70 comprises the pellet flotation cylinder 76 internally having the entrapping immobilization pellets 74 each in the shape of a star, heart, etc. in place of the filter unit 46 internally having the entrapping immobilization pellets 44 of the present invention.

As shown in FIG. 11, the pellet flotation cylinder 76 is formed as a transparent cylindrical container 77 (purification tank). A plurality of slit holes 78 (intake ports and return ports) to take in and return breeding water are formed on the side surface of the cylinder, and an air pump 18 to supply air into the pellet flotation cylinder 76 is connected to the side surface. Aquarium lighting (not shown) may also be placed on the bottom of the pellet flotation cylinder 76.

Lighting of various colors such as a fluorescent lamp, an incandescent lamp, LED, or black light may be used as the aquarium lighting without specific limitations.

The amount of the entrapping immobilization pellets 74 introduced may be the same as in the first embodiment.

Next, the action of the aquarium set 70 of the present embodiment will be described.

First, air is supplied into the pellet flotation cylinder 76 by the air pump 18. This generates a circulating water flow (arrow) from down to up in the pellet flotation cylinder 76. Breeding water is taken in the pellet flotation cylinder 76 from the aquarium 12 through the slit holes 78.

Here, ammonium nitrogen contained in the breeding water is decomposed and removed by the action of nitrifying bacteria in the entrapping immobilization pellets 74 in the pellet flotation cylinder 76. The entrapping immobilization pellets 74 having various colors and shapes are floated together with the circulating water flow in the pellet flotation cylinder 76 at the same time.

The breeding water after purification in the pellet flotation cylinder 76 is returned to the aquarium 12 through the slit holes 78.

A circulating water flow from down to up is generated in the pellet flotation cylinder 76 by a flow of air supplied from the air pump 18. The entrapping immobilization pellets have a gravity extremely close to that of water, so that the pellets floated wavering. Further, the pellets are themselves beautiful and worth watching and improve the beauty of the whole aquarium. In particular, the entrapping immobilization pellets dyed with a dye not impairing transparence, a fluorescent paint, a luminous paint, lame powder having metallic luster, or the like are floated wavering in the pellet flotation cylinder 76 while glowing with light from aquarium lighting, and can express a change in color or light. Further, the entrapping immobilization pellets dyed with a luminous paint are floated in the pellet flotation cylinder 76 while slightly glowing even in the dark and can create a fantastic mood. Further, the entrapping immobilization pellets each formed into various shapes such as a star shape, heart shape, and doll shape can realize a sense of season or a landscape in the main body or periphery of the aquarium.

The present embodiment is described taking an example in which the pellet flotation cylinder 76 is placed in the aquarium 12; however, the present embodiment is not limited to this example, and it is possible to place the pellet flotation cylinder 76 outside the aquarium 12.

Figure 12:
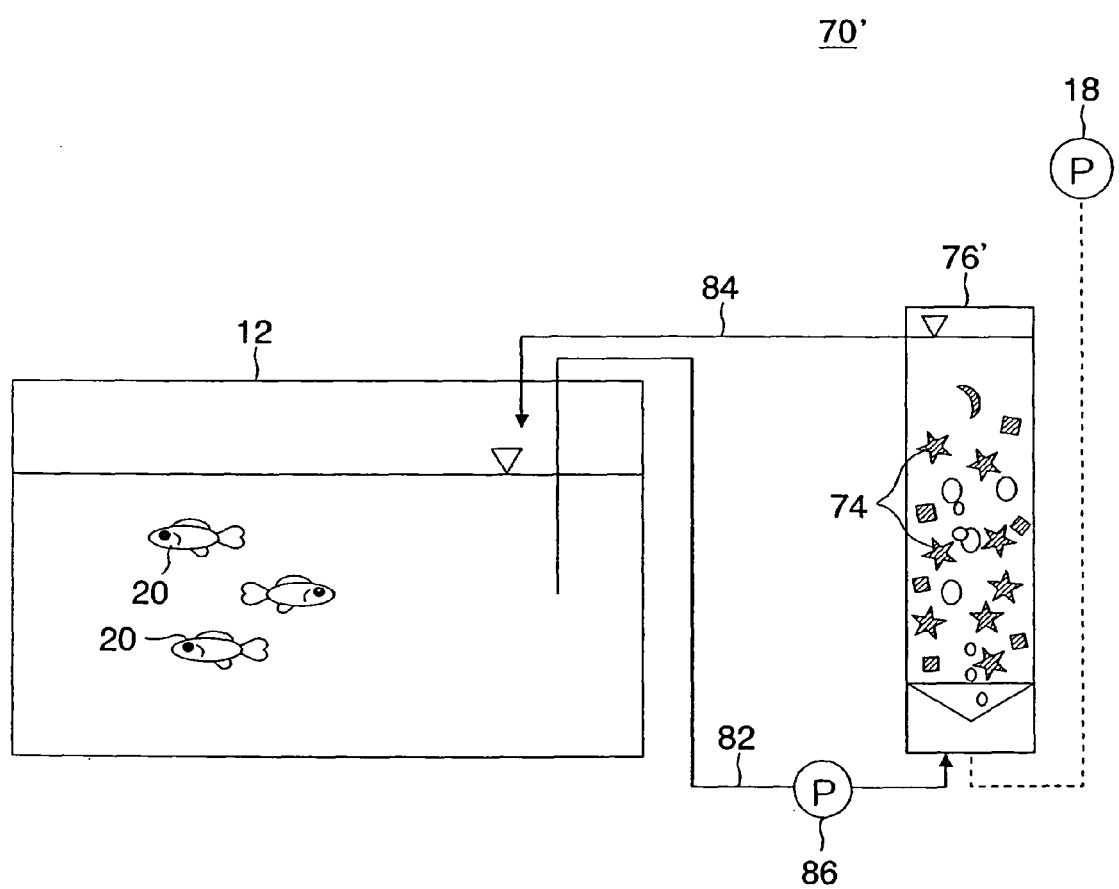
FIG. 12 is a view describing a modification of FIG. 11.
Figure 13:
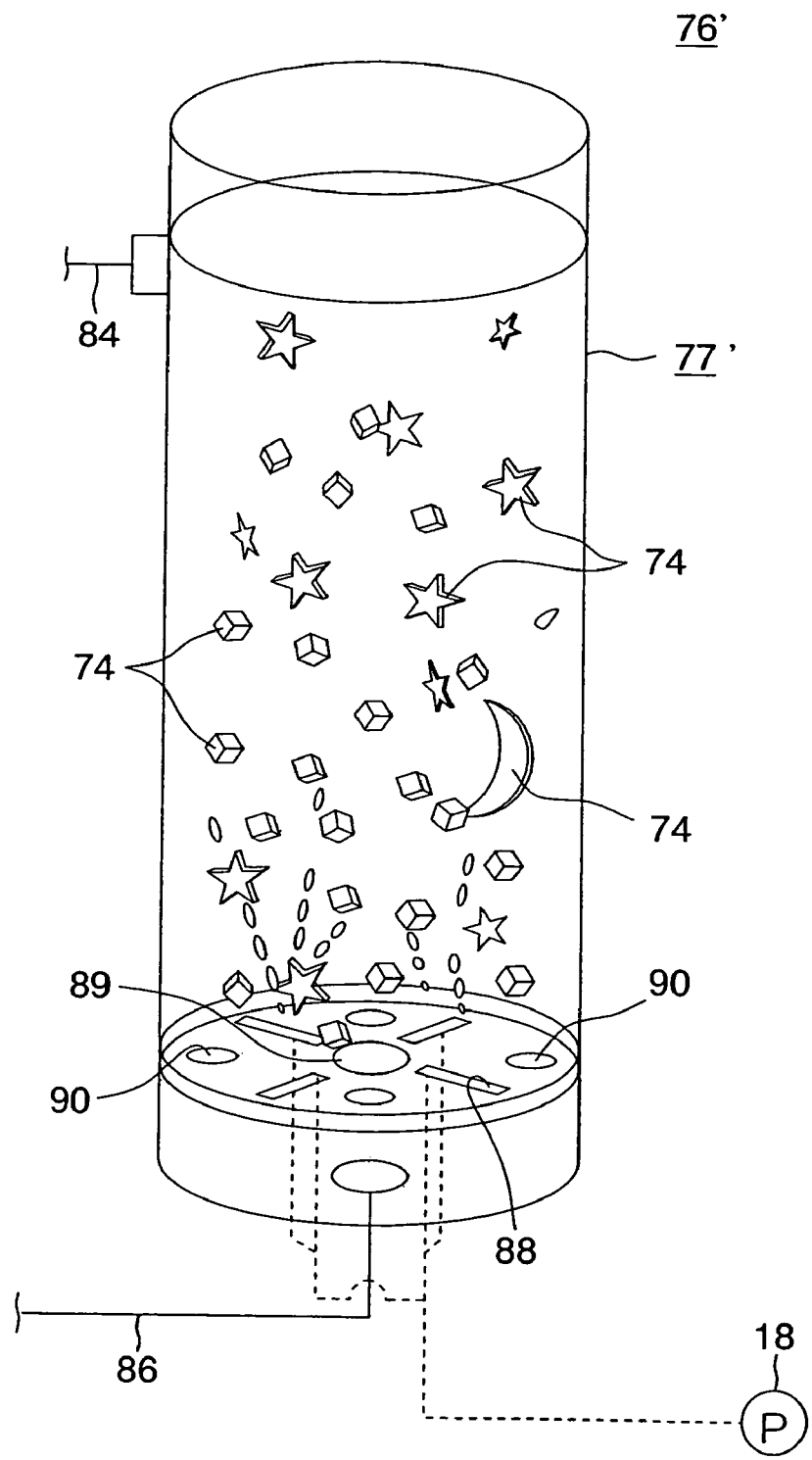
FIG. 13 is an oblique view describing a purification apparatus of FIG. 12.

FIG. 12 is a view describing an aquarium set 70' which is a modification of FIG. 11 and in which a pellet flotation cylinder 76' is placed outside an aquarium 12. FIG. 13 is an oblique view showing a configuration of the pellet flotation cylinder 76' of FIG. 12.

As shown in FIG. 12, the aquarium set 70' comprises, as main components, the aquarium 12; the pellet flotation cylinder 76' as a transparent tank; an intake pipe 82 to make the inside of the aquarium 12 communicate with an intake port (not shown) of the pellet flotation cylinder 76'; a return pipe 84 to make a return port (not shown) of the pellet flotation cylinder 76' communicate with the inside of the aquarium 12; and a circulation pump 86 (circulation device) to circulate breeding water between the aquarium 12 and the pellet flotation cylinder 76'.

As shown in FIG. 13, the pellet flotation cylinder 76' is formed as a transparent cylindrical container 77' (purification tank), and an air outlet port 88 to which air is supplied; an intake port 89 for breeding water; and a fluorescent lamp 90 as aquarium lighting are provided on the bottom of the pellet flotation cylinder 76'. The air outlet port 88 is connected to an air pump 18, and the intake port 89 communicates with an intake pipe 86. The shape, location, and the like of the air outlet port 88, intake port 89, or fluorescent lamp 90 are not limited to those in FIG. 13.

In such a configuration, breeding water is taken in the pellet flotation cylinder 76' from the aquarium 12 through the intake pipe 82 by the circulation pump 86. On the other hand, air is supplied into the pellet flotation cylinder 76' by the air pump 18. Ammonium nitrogen or the like contained in the breeding water is decomposed and removed by the entrapping immobilization pellets 74 in the pellet flotation cylinder 76'. The breeding water after purification is returned to the aquarium 12 from the return port in the pellet flotation cylinder 76' through the return pipe 84.

Accordingly, the aforementioned effect of the present embodiment can be exhibited, and furthermore the pellet flotation cylinder can be used in combination with an aquarium and can also be used as an ornamental (object d'art) which realizes the beauty.

According to the entrapping immobilization pellets for purifying breeding water, the process and the apparatus for purifying breeding water, and the aquarium set (first, second, and third embodiments) according to the present invention as described above, the entrapping immobilization pellets can exhibit purification performance immediately after being placed in an aquarium, and furthermore can provide a color, luster, and the like for the main body or periphery of the aquarium to improve the beauty of the whole aquarium environment.

The present embodiment shows an example in which the entrapping immobilization pellets are used as colored and formed into various shapes; however, it is obviously possible to use a combination of two or more types of the entrapping immobilization pellets formed into a common substantially cubic shape, the entrapping immobilization pellets containing an algaecide, the entrapping immobilization pellets containing a pH indicator, and the like. The entrapping immobilization pellets formed into various shapes may also contain at least one of the algaecides, pH indicators, and colorants.

Various embodiments of the entrapping immobilization pellets for purifying breeding water, the process and the apparatus for purifying breeding water, and the aquarium set according to the present invention are as described above; however, the present invention is not limited to the above embodiments, and various embodiments are possible.

For example, the pellet flotation cylinder of the third embodiment is described taking a case where aquarium lighting is provided; however, the beauty of the cylinder can be sufficiently improved even if aquarium lighting is not provided (natural light is used, for example). It is also possible to place aquarium lighting in the purification material, the simple purification apparatus, and the purification apparatus in the first and second embodiments.

The present embodiment is described for a process of purifying breeding water using the entrapping immobilization pellets in which nitrifying bacteria are immobilized; however, the present embodiment is not limited to such a process, and it is possible to use the entrapping immobilization pellets colored, where anaerobic microorganisms (such as anaerobic ammonium oxidizing bacteria or denitrifying bacteria) are immobilized, in an apparatus for purifying breeding water maintained to be anaerobic. In this case, it is preferable to aerate breeding water purified in the anaerobic purification apparatus to make the water aerobic, and then return the water to an aquarium. This can further decompose and denitrify nitrate nitrogen in the breeding water.

The present embodiment is described taking an example in which the entrapping immobilization pellets are used as relatively small pellets; however, the present embodiment is not limited to this example, and the entrapping immobilization pellets may be formed modeled in the shape of a water plant, gravel, stone, shell, or the like and used as accessories that can be placed in an aquarium.

In the present embodiment, the entrapping immobilization pellets of the present invention can be applied to a commercially available external filter unit or the like which is not described above for the present embodiment.

The present invention is applied to an ornamental aquarium in the present embodiment; however, the present invention can be applied not only to an ornamental aquarium but also to an aquarium for aquaculture in a pond or the like, an aquarium for transportation, an aquarium for an Aquarium, or the like.

EXAMPLES

Next, the present invention will be described in more detail below with reference to examples; however, the present invention is not limited to the following examples.

Example 1

Water purification tests using the entrapping immobilization pellets 14 of the present invention (Example 1) and conventional pellets (Comparative Example 1) were carried out as follows using the simple purification apparatus 17 of FIG. 5.

<Equipment outline>
(1) Aquarium
  Aquarium size: 30 cm×20 cm×20 cm (about 15 L)
(2) Simple Purification Apparatus
  Bacter Cel System Rotor (manufactured by GEX) *Filter media were not used in the examples.
  (Example 1) 15 mL of the entrapping immobilization pellets 14 of the present invention were included in the rotation drum 24.
  (Comparative Example 1) 15 mL of conventional attachment pellets were included in the rotation drum 24.
(3) Other Equipment
  Diffuser (Air Stone)
  Gravel not used
  Temperature control unit (ceramic heater having an automatic temperature controller)
  Wool mats were placed in the upper filter and the bottom filter.

<Breeding Conditions>
  Feed: Commercially available feed for ornamental fish (Hikari Crest Characin:
    manufactured by Kyorin Co., Ltd.)
  Feeding: Once per day, 0.1 g per feeding (nitrogen load: 0.527 mg-N/L/day)
  Water Temperature: 25° C.
  Ornamental fish: 30 neon tetra (dead fish removed from the aquarium and not supplemented)
  Others: Water not exchanged, algaecide not added <Objects of Evaluation>
(1) The entrapping immobilization pellets 14 of the present invention (Examples) The colored entrapping immobilization pellets were produced by the aforementioned process for producing the entrapping immobilization pellets.

(Composition of Entrapping Immobilization Pellets 14)
  Sludge: Purified water sludge (dewatered sludge)
  Sludge concentration: 2 mass %/pellet
  Colorant: Dye for dyeing resin, 0.02 mass %
  Immobilizing material: Polyethylene glycol diacrylate, 5 mass %
  Polymerization promoter: N,N,N',N'-tetramethylethylenediamine, 0.0500 mass %
  Polymerization initiator: Potassium persulfate, 0.0025 mass %

(2) Conventional attachment pellets (Comparative Examples)
  Commercially available sponge pellets for ornamental fish <Evaluation Method>
  Water quality change in breeding water
  $NH_4$—N (ammonium nitrogen): $NH_4$ meter (frequency: once per day)
  Nox—N (nitrate nitrogen, nitrite nitrogen): NOx meter (frequency: once per day)

Figure 14A:
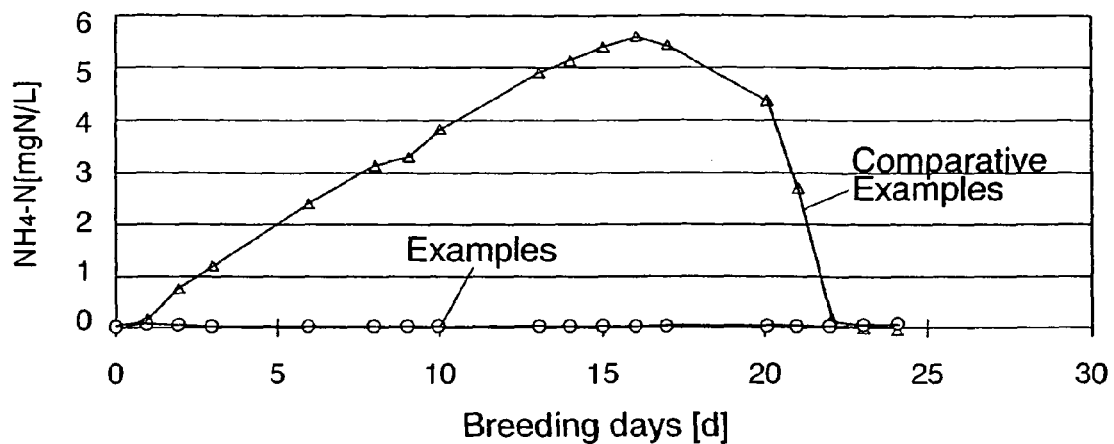
FIGS. 14A to 14C are graphs for the example.
Figure 14B:
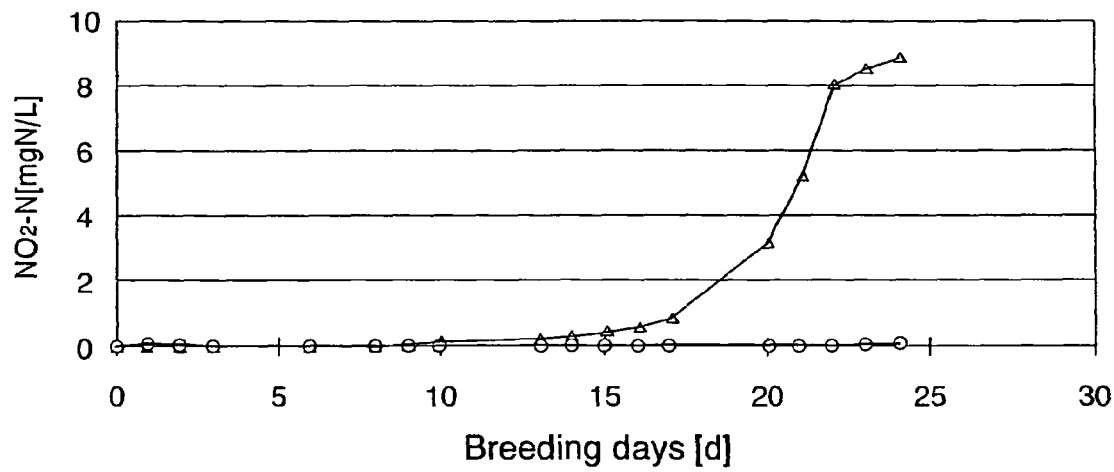
Figure 14C:
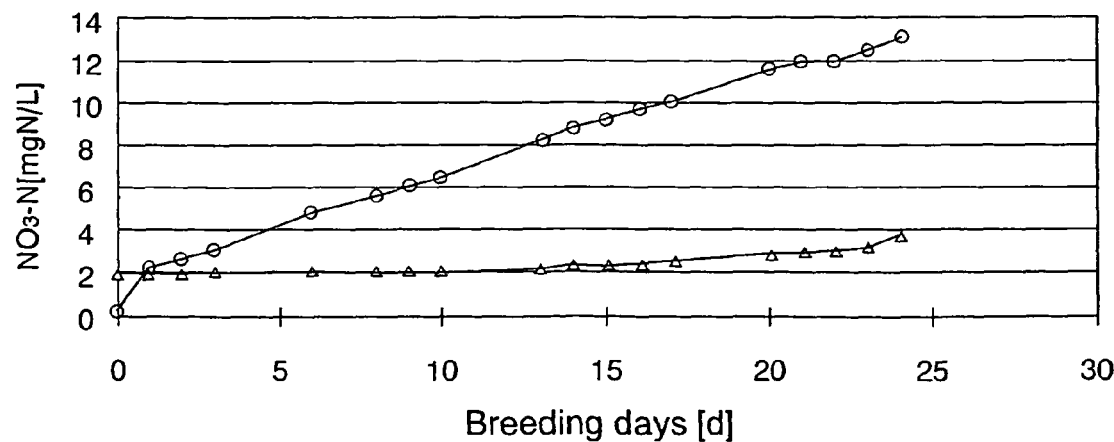

<Evaluation Results>
(1) Water Quality Change in Breeding Water
FIGS. 14A to 14C are graphs showing the results of change over time in the quality of breeding water. In FIGS. 14A to 14C, FIG. 14A is a graph showing a change in the concentration of ammonium nitrogen in breeding water; FIG. 14B is a graph showing a change in the concentration of nitrite nitrogen in breeding water; and FIG. 14C is a graph showing a change in the concentration of nitrate nitrogen in breeding water.

It was found as shown in FIGS. 14A to 14C that in Example 1 using the entrapping immobilization pellets 14 of the present invention, the amounts of ammonium nitrogen and nitrite nitrogen were extremely close to zero, respectively, since the initial stage of introduction of the entrapping immobilization pellets 14. It was found that accordingly, the amount of nitrate nitrogen generated by oxidation decomposition of the ammonium nitrogen and nitrite nitrogen was increased since the initial stage of introduction of the pellets.

On the other hand, as shown in FIGS. 14A to 14C, in Comparative Example 1 using conventional pellets, the amount of ammonium nitrogen was not reduced and continuously increased until about two weeks passed since introduction of the pellets. Thereafter, the amount of ammonium nitrogen was gradually reduced, and the amount of nitrite nitrogen, which was almost zero until that time, started to be drastically increased. It was found that accordingly, the amount of nitrate nitrogen was almost not increased since the initial stage of introduction of the pellets.

It was found from above that since nitrifying bacteria (ammonium oxidizing bacteria or nitrite oxidizing bacteria) are previously entrapped and immobilized in the entrapping immobilization pellets of the present invention, nitrite generated by oxidizing ammonium is rapidly oxidized to nitrate. It was found that accordingly, accumulation of ammonium nitrogen and nitrite nitrogen can be suppressed immediately after the entrapping immobilization pellets are introduced into an aquarium, and thus water quality favorable for breeding ornamental fish can be provided.

Examples 2 and 3

Next, water purification tests were carried out using activated sludge (Example 2) and purified water sludge (Example 3) in the entrapping immobilization pellets of the present invention and not using pellets (Comparative Example 2).

In the Examples, the tests were carried out using the same equipment and breeding conditions as in Example 1, except that 35 neon tetra (15 large fish and 20 small fish) were bred, commercially available Rotor Boy M (manufactured by GEX, not provided with sponge filter media) was used as a purification apparatus, and an upper filter and a bottom filter were not used.

Evaluation was performed by the same evaluation method as in Example 1 and furthermore by the following method for the pH, DO (dissolved oxygen), and TOC of breeding water, the generation state of algae, and the number of remaining neon tetra. Specifically, the pH of breeding water was measured once per day by a pH sensor, and the DO of breeding water was measured once per day by a DO sensor. The TOC of breeding water was measured at a frequency of once per week by a TOC meter. The generation state of algae was visually evaluated (frequency: once per day). The number of remaining neon tetra was visually evaluated (frequency: once per day).

<Evaluation Results>

In Examples 2 and 3 using the entrapping immobilization pellets 14 of the present invention, a small amount of algae was generated about 16 days after the start of breeding, and the amount of algae was further increased after about 28 days. While the inside of the aquarium 12 could be barely watched in Example 2, neon tetra in the aquarium 12 could be watched with almost no difficulty in Example 3.

On the other hand, in Comparative Example 2 not using pellets, a large amount of algae was generated about 16 days after the start of breeding, and a further large amount of algae was generated after about 28 days. The inside of the aquarium 12 could almost not be seen, and neon tetra could not be watched.

It was found from above that generation of algae can be suppressed using, in the entrapping immobilization pellets 14 of the present invention, purified water sludge having a small content of phosphorus that is a cause of eutrophication of water.

Figure 15A:
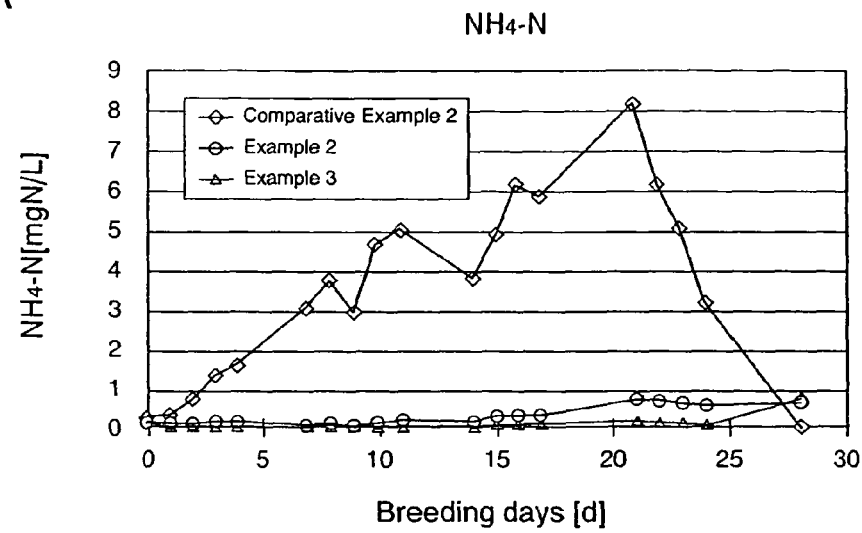
FIGS. 15A to 15C are graphs for the example.
Figure 15B:
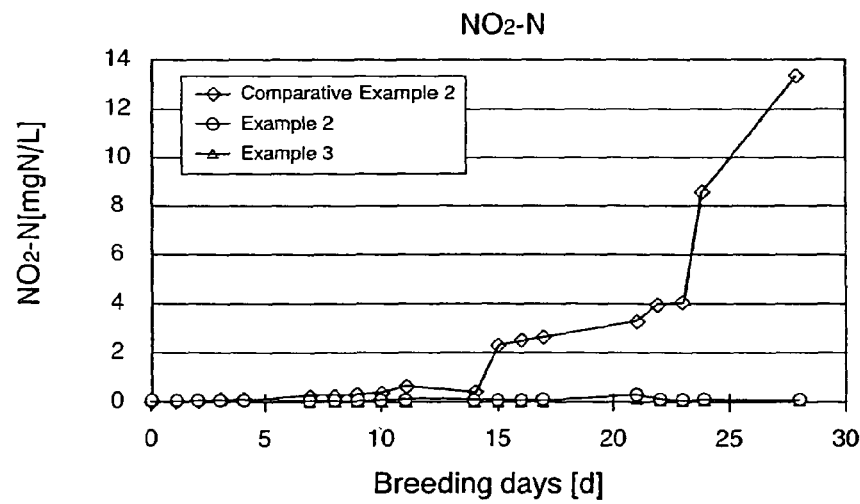
Figure 15C:
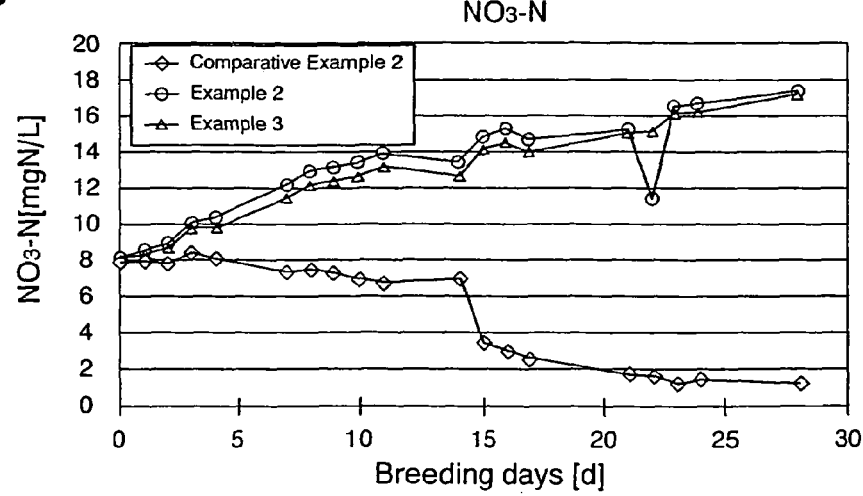

FIGS. 15A to 15C are graphs showing the results of change over time in the quality of breeding water. In FIGS. 15A to 15C, FIG. 15A is a graph showing a change in the concentration of ammonium nitrogen in breeding water; FIG. 15B is a graph showing a change in the concentration of nitrite nitrogen in breeding water; and FIG. 15C is a graph showing a change in the concentration of nitrate nitrogen in breeding water.

As shown in the figure, in Examples 2 and 3 using the entrapping immobilization pellets 14 of the present invention, the amounts of ammonium nitrogen and nitrite nitrogen were extremely close to zero, respectively, since the initial stage of introduction of the entrapping immobilization pellets 14, and the pellets exhibited purification performance since the initial stage of introduction of the pellets. In particular, it was found as shown in FIG. 15A that the entrapping immobilization pellets of Example 3 using purified water sludge have ammonium nitrogen removing performance higher than that of the entrapping immobilization pellets of Example 2 using activated sludge.

On the other hand, in Comparative Example 2 not using pellets, the amount of ammonium nitrogen was not reduced and continuously increased and the water quality deteriorated until about 16 days passed.

It was confirmed from above that ammonium nitrogen and the like contained in breeding water are surely removed by the entrapping immobilization pellets of the present invention.

Figure 16:
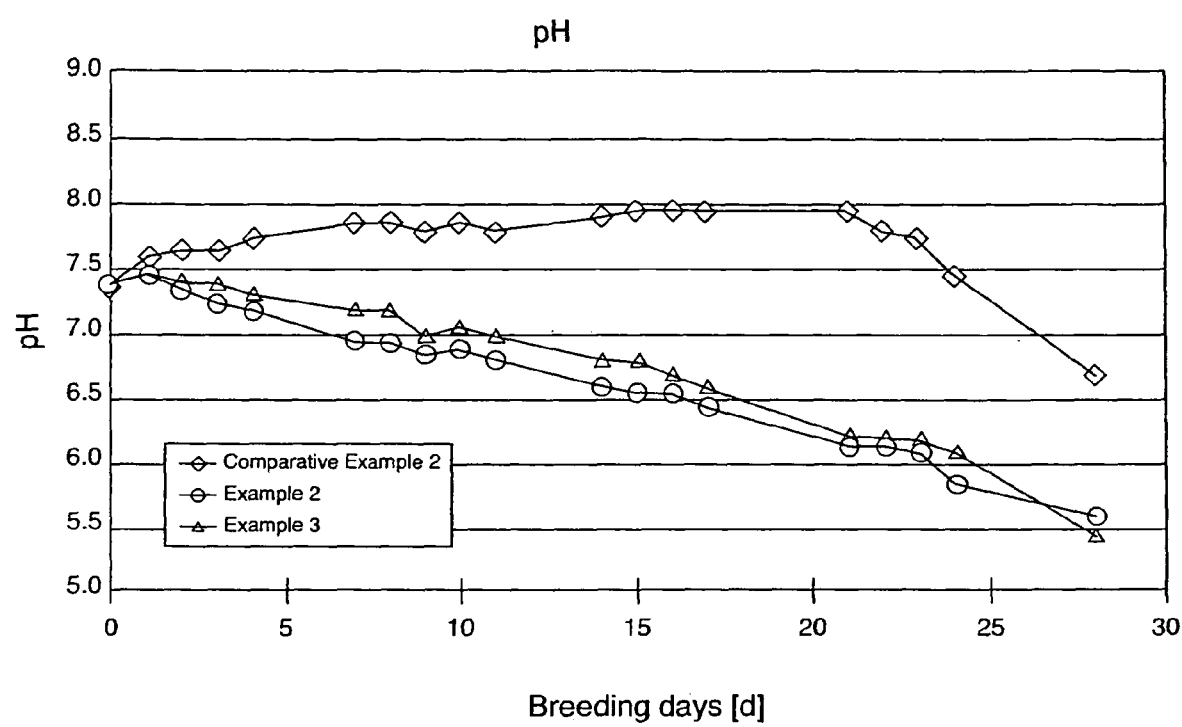
FIG. 16 is a graph for the example.
Figure 17:
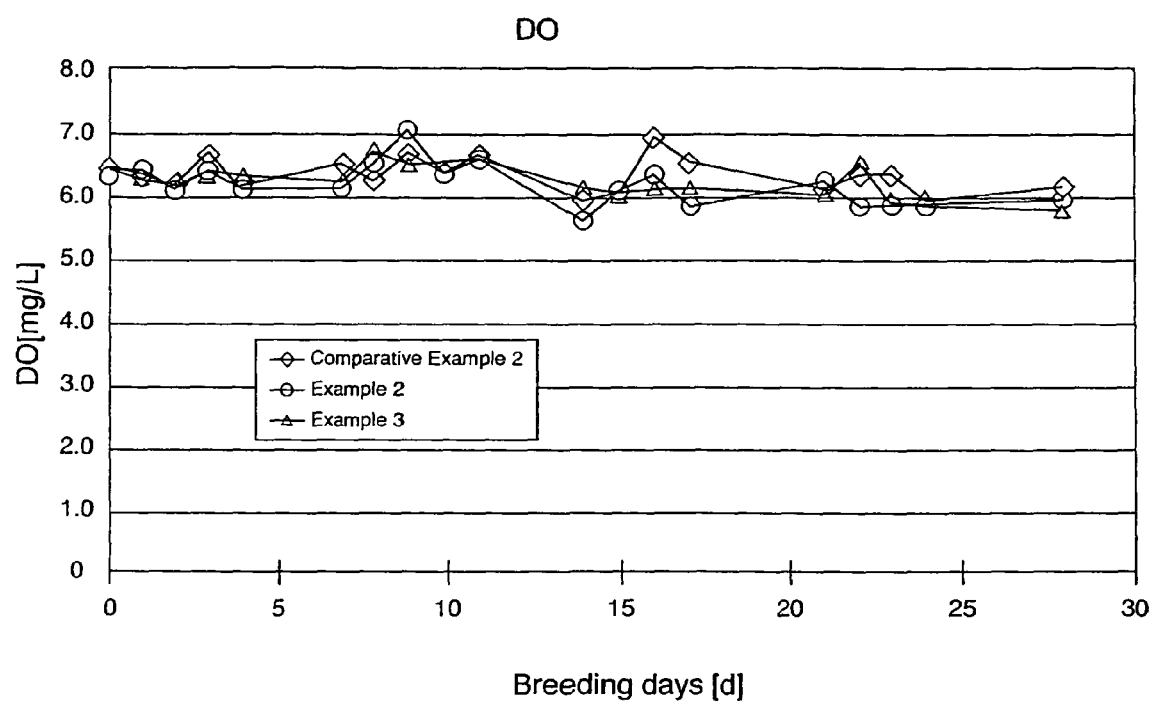
FIG. 17 is a graph for the example.

FIG. 16 is a graph showing the results of change over time in the pH of breeding water. FIG. 17 is a graph showing the results of change over time in the DO of breeding water.

As shown in FIG. 16, in Examples 2 and 3 using the entrapping immobilization pellets 14 of the present invention, the pH was reduced almost in the same manner. This is because ammonium nitrogen in breeding water is decomposed by oxidation by nitrifying bacteria in the entrapping immobilization pellets to increase the amount of nitrate nitrogen, and the entrapping immobilization pellets are shown to have high purification performance.

As shown in FIG. 17, in Examples 2 and 3 using the entrapping immobilization pellets 14 of the present invention, the degree of change over time in the DO was small and the same as in Comparative Example 2.

It was confirmed from above that the entrapping immobilization pellets of the present invention can surely remove ammonium nitrogen and the like contained in breeding water, and therefore the amount of dissolved oxygen necessary for breeding ornamental fish is not reduced, and good water quality can be maintained for ornamental fish.

Figure 18:
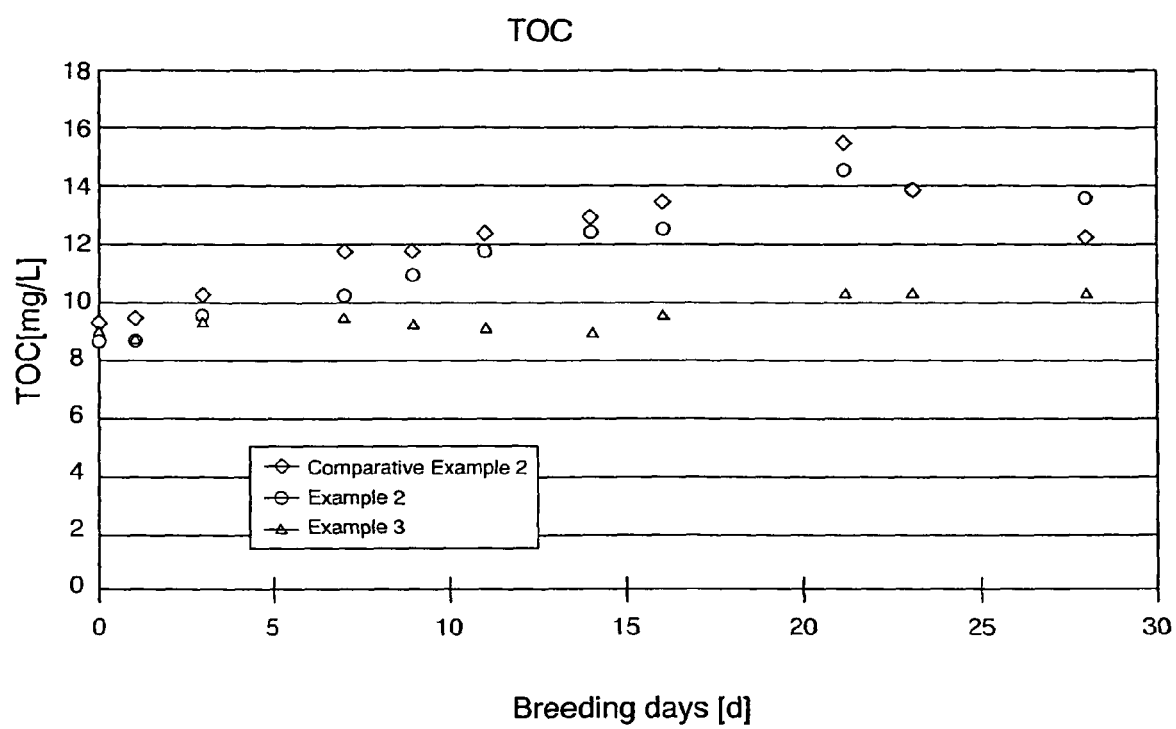
FIG. 18 is a graph for the example.

FIG. 18 is a graph showing the results of change over time in the TOC of breeding water.

As shown in the figure, in Examples 2 and 3 to which the present invention was applied, the TOC value remained to be lower than in Comparative Example 2 until 20 days passed since the start of breeding. In particular, it was found that in Example 3 using purified water sludge, the TOC value remained to be lower than in Comparative Example 2 even one week after the start of breeding.

It was found from above that microorganisms in the entrapping immobilization pellets of the present invention decompose not only ammonium but also an organic substance in breeding water and can maintain good water quality.

Figure 19:
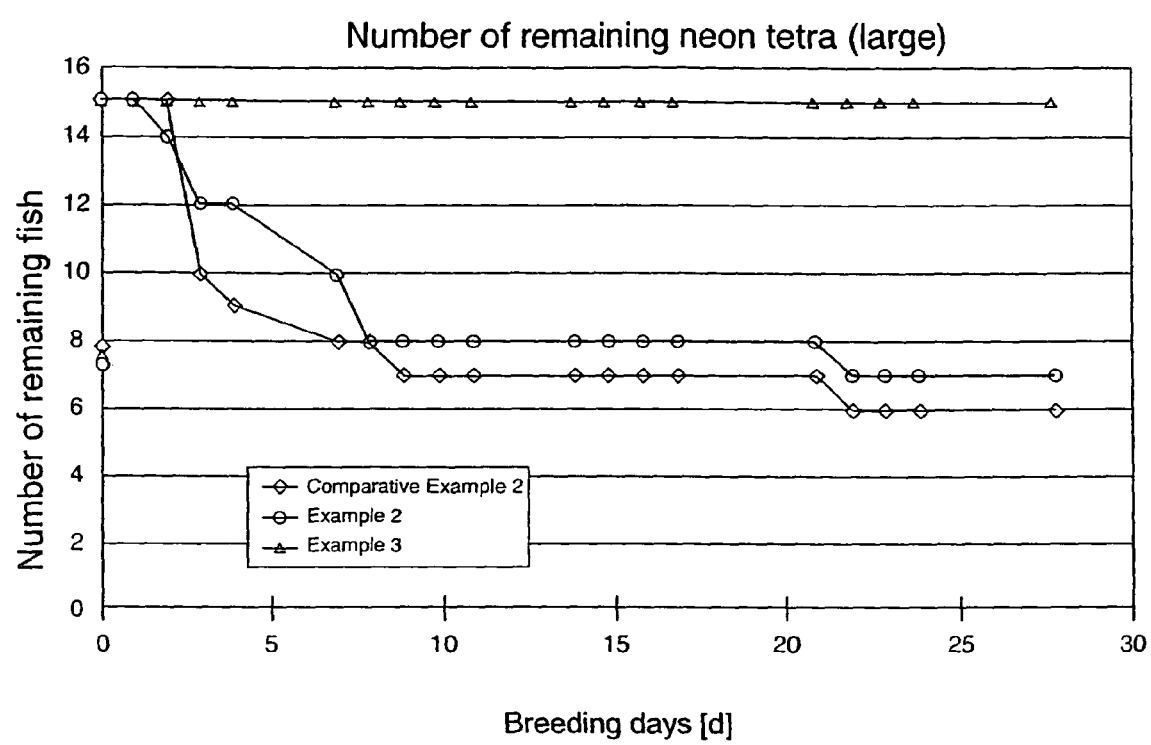
FIG. 19 is a graph for the example.

FIG. 19 is a graph showing the member of remaining neon tetra (large, 15 fish).

It was found as shown in the figure that in Examples 2 and 3 using the entrapping immobilization pellets 14 of the present invention, the number of remaining neon tetra was larger than in Comparative Example 2 not using pellets. In particular, in Example 3 using purified water sludge, no fish was dead over 28 days and the effect of the pellets was significant.

It was confirmed from above that the entrapping immobilization pellets of the present invention, in particular, the entrapping immobilization pellets using purified water sludge can exhibit water purification performance since the initial stage of introduction of the pellets and can maintain water quality highly favorable for ornamental fish.

What is claimed is:

1. Entrapping immobilization pellets for purifying breeding water in an aquarium to breed aquatic animals,
wherein the entrapping immobilization pellets have a phosphorus content of 0.05 mass % or less, the entrapping immobilization pellets contain an algaecide, and the entrapping immobilization pellets formed with a microorganism within the entrapping immobilization pellets.

2. The entrapping immobilization pellets for purifying breeding water according to claim 1, wherein the microorganisms contained in the entrapping immobilization pellets are nitrifying bacteria.

3. An aquarium set comprising: the entrapping immobilization pellets according to claim 2 in an aquarium to breed aquatic animals.

4. A process for purifying breeding water in an aquarium to breed aquatic animals, the process comprising:
bringing the breeding water to breed aquatic animals into contact with the entrapping immobilization pellets according to claim 1 to purify the breeding water.

5. An apparatus for purifying breeding water in an aquarium to breed aquatic animals, the apparatus comprising:
a transparent purification tank having an intake port to take in breeding water in the aquarium and a return port to return the purified breeding water into the aquarium;
the entrapping immobilization pellets according to claim 1 provided in the purification tank; and
an air supply device to supply air into the purification tank.

6. The apparatus for purifying breeding water according to claim 5, wherein aquarium lighting is provided in the purification tank.

7. An aquarium set comprising:
an aquarium to breed aquatic animals;
the purification apparatus according to claim 6 placed outside the aquarium;
an intake pipe that makes the inside of the aquarium communicate with the intake port of the purification apparatus to take in the purification apparatus breeding water in the aquarium;
a return pipe that makes the return port of the purification apparatus communicate with the inside of the aquarium to return into the aquarium the breeding water purified in the purification apparatus; and
a circulation device to circulate the breeding water between the aquarium and the purification apparatus.

8. An aquarium set comprising: the purification apparatus according claim 5 placed in an aquarium to breed aquatic animals.

9. An aquarium set comprising:
an aquarium to breed aquatic animals;
the purification apparatus according to claim 5 placed outside the aquarium;
an intake pipe that makes the inside of the aquarium communicate with the intake port of the purification apparatus to take in the purification apparatus breeding water in the aquarium;
a return pipe that makes the return port of the purification apparatus communicate with the inside of the aquarium to return into the aquarium the breeding water purified in the purification apparatus; and
a circulation device to circulate the breeding water between the aquarium and the purification apparatus.

10. An aquarium set comprising: the entrapping immobilization pellets according to claim 1 in an aquarium to breed aquatic animals.

11. The entrapping immobilization pellets for purifying breeding water according to claim 1, wherein the entrapping immobilization pellets have an algaecide content of 0.01 to 3 mass %.

* * * * *